(12) United States Patent
Hart et al.

(10) Patent No.: US 6,261,567 B1
(45) Date of Patent: *Jul. 17, 2001

(54) OVERCOMING INTERFERENCE IN ALPHAVIRUS IMMUNE INDIVIDUALS

(75) Inventors: Mary Katherine Hart, Frederick; Maryam Azarion, Damascus, both of MD (US)

(73) Assignee: The United States of America as represented by the Secretary of the Army, Washington, DC (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/082,357

(22) Filed: May 20, 1998

Related U.S. Application Data

(60) Provisional application No. 60/077,731, filed on Mar. 12, 1998, and provisional application No. 60/047,167, filed on May 20, 1997.

(51) Int. Cl.[7] .......................... A61K 39/12; A61K 39/193; A61K 39/295; A61K 31/711
(52) U.S. Cl. ..................................... 424/199.1; 424/218.1; 514/44
(58) Field of Search .............................. 424/218.1, 202.1, 424/199.1; 514/44

(56) References Cited

U.S. PATENT DOCUMENTS 4,722,848 * 2/1988 Paoletti et al. .................... 424/199.1

OTHER PUBLICATIONS

Davis et al. Virology 212:102–110, 1995.*
McClain et al. Journal of Infectious Diseases 177:634–41, 1998.*
Strauss et al. Microbiological Reviews 58:491–562, 1994.*

* cited by examiner

*Primary Examiner*—Mary E. Mosher
(74) *Attorney, Agent, or Firm*—Elizabeth Arwine; Charles H. Harris

(57) ABSTRACT

In this application is described a method for overcoming alphavirus vaccine interference in alphavirus-immune subjects by administration of a second alphavirus vaccine which is altered such that it is not accessible to interfering antibodies. Examples of such alterations are described as well as evidence showing that alphavirus interference likely results from the binding of interfering antibodies to viral proteins expressed on infected cells thereby causing lysis of infected cells.

30 Claims, 7 Drawing Sheets

TC-83

[PE2]=[E1]

GLYCOPROTEIN HETERODIMERS FORM IN ER AND ARE TRANSPORTED TO GOLGI

[E3] RKRR [E2]=[E1]
↑
FURIN

THE PE2 GLYCOPROTEIN IS CLEAVED TO FORM E2-E1 HETERODIMERS IN THE TC-83 VACCINE. THREE E2-E1 HETERODIMERS ASSOCIATE TO FORM ONE VIRUS SPIKE. TC-83 HAS 5 AA CHANGES IN E2 AND 2 AA CHANGES IN E1 GLYCOPROTEINS FROM THE VIRULENT PARENT STRAIN.

V3526

[PE2]=[E1]

THE PE2 CLEAVAGE SITE IS DELETED IN V3526. VIRUS SPIKES ARE COMPRISED OF THREE PE2-E1 HETERODIMERS. ONE AMINO ACID CHANGE AT E1:253 IS ALSO PRESENT.

OVERCOMING INTERFERENCE IN ALPHAVIRUS IMMUNE INDIVIDUALS

This application claims priority to provisional applications Ser. No. 60/047,167, filed May 20, 1997, and 60/077,731, filed Mar. 12, 1998.

INTRODUCTION

Venezuelan (VEE), Eastern (EEE), and Western (WEE) equine encephalitis alphaviruses are endemic to North and South America. They present potential medical threats to equines and people. Clinical symptoms of illness include fever, headache, photophobia, seizures, and encephalitis.

it does not induce longlasting mucosal immunity [Hart, M. K. et al. (1997) *Vaccine* 15: 363–369]. Therefore, it is not a suitable alternative to TC-83 vaccination.

Since immunity to one alphavirus does not protect animals adequately from subsequent exposure to a virulent heterologous alphavirus [Casals, J. (1963) *Am. J. Trop. Med. Hyg.* 12: 587–596], there is a need for a method to overcome alphavirus interference, and a vaccine which is able to bypass interference.

TABLE 1

Investigational New Drug (IND) Alphavirus Vaccines Used in this Study

| Vaccine | Virus | Antigen Form | Dose[1] (PFU)[2] | Schedule | Booster |
|---|---|---|---|---|---|
| CHIK | Chickungunya (CHIK) | live-attenuated | 0.5 ml ($10^5$ PFU) | day 0 | Not available |
| TC-83 | Venezuelan equine encephalitis (VEE) | live-attenuated | 0.5 ml ($10^4$ PFU) | day 0 | 0.5 ml of C-84 |
| C-84 | VEE | formalin-inactivated | 5.58 µg/0.5 ml dose | day 0, 7, 28 | |
| V3526[3] | VEE (vaccine candidate) | live-attenuated | 0.5 ml ($10^4$ PFU) | day 0 | Not available |
| EEE | Eastern equine encephalitis (EEE) | formalin-inactivated | 1.84 µg/0.5 ml dose | day 0, 28 | 0.5 ml |
| WEE | Western equine encephalitis (WEE) | formalin-inactivated | 0.83 µg/0.5 ml dose | day 0, 7, 28 | 0.5 ml |

[1]Protein concentrations for C-84, EEE, and WEE were determined by Mike Shoemaker (unpublished observations, 1996).
[2]Plaque forming units (PFU).
[3]V3526 vaccine candidate is under development and has not been approved for human use yet.

Currently, live or formalin-inactivated vaccines are used under Investigational New Drug (IND) status to immunize at-risk personnel. For VEE virus, a live-attenuated TC-83 vaccine [Alevizatos, A. C. et al. (1967) *Am. J. Trop. Med. Hyg.* 16: 762–768; Berge, T. O. et al. (1961) *Am. J. Hyg.* 73: 209–218] and a formalin-inactivated C-84 vaccine [Cole, F. E. et al. (1974) *Appl. Micro.* 27: 150–153] are available. In addition, a new vaccine candidate V3526 [Davis, N. L. et al. (1995) *Virology* 212: 102–110] is under investigation. For EEE [Bartelloni, P. J. et al. (1970) *Am. J. Trop. Med. Hyg.* 19: 123–126] and WEE [Bartelloni, P. J. et al. (1971) *Am J. Trop. Med. Hyg.* 20: 146–149] viruses, formalin-inactivated IND vaccines are available. Although TC-83 has been used to control equine epizootics, most commonly used veterinary vaccines are inactivated products (please see Table 1 for alphavirus vaccines available).

The current alphavirus vaccines have several limitations, including the observation in horses [Calisher, C. H. et al. (1973) *Appl. Microl.* 26: 485–488] that prior immunity to EEE or WEE viruses interferes with the induction of protective immune responses to subsequent vaccination with the live-attenuated VEE vaccine TC-83. Interference may be mediated by cross-reactive, non-neutralizing (in plaque assay) antibodies that presumably inhibit viral replication of live-attenuated vaccine strains. The inability to induce virus-neutralizing antibodies to VEE virus in alphavirus-immune animals or people significantly limits the usefulness of the current live-attenuated TC-83 vaccine. The formalin-inactivated C-84 vaccine does not replicate and appears to be less susceptible to interference. However, C-84 is currently used only as a booster vaccine because it does not induce adequate protection in hamsters [Jahrling, P. B. and Stephenson, E. H. (1984) *J. Clin. Microbiol.* 19: 429–431], it requires multiple inoculations and periodic boosters, and

SUMMARY OF THE INVENTION

The present invention satisfies the need discussed above. The present invention relates to a method and composition for overcoming alphavirus interference.

Vaccine interference prevents the induction of protective immune responses to live attenuated alphavirus vaccines in animals or people with pre-existing immunity to other alphaviruses. Cross-reactive, non-neutralizing antibodies may mediate interference by inhibiting replication of the vaccine strain after infection of susceptible cells by binding to glycoproteins on infected cells and causing lysis. The new VEE vaccine candidate, V3526, was developed [Davis, N. L. et al. (1995), supra] using site-directed mutagenesis to incorporate desired mutations into a full-length infectious clone. V3526 contains a cleavage site deletion in the precursor E2 (PE2) glycoprotein sequence and a viability-restoring mutation at glycoprotein E1:253. These mutations result in a virion that has glycoprotein spikes containing three uncleaved PE2-E1 heterodimers instead of the three cleaved E2-E1 heterodimers normally present in VEE viruses, including the TC-83 strain (Please see FIG. 1 for an illustration of the changes in V3526).

We hypothesized that these mutations may alter the sequence, conformation and/or accessibility of cross-reactive epitopes such that cross-reactive antibodies could no longer bind the glycoproteins during viral replication. In the absence of binding by cross-reactive interfering antibodies, V3526 should induce similar neutralizing antibody titers in naive or alphavirus-immune recipients. This would overcome the problem of vaccine interference in alphavirus-immune individuals.

We found that prior EEE vaccination with a formalin-inactivated product did not adversely affect production of protective immunity against VEE after immunization with V3526. Similar results were seen when the first alphavirus vaccine was a live-attenuated Chikungunya vaccine, as opposed to a reduction in titers of neutralizing antibodies induced to the live-attenuated VEE product, TC-83.

In addition, a monoclonal antibody, K42, reactive with Sindbis virus E1 glycoprotein and which cross-reacts with different alphaviruses [Wang, K.-S. et al. (1991) *Virology* 181: 694–702] was shown to interfere with neutralizing antibody responses to TC-83, but not to V3526, when the monoclonal antibody was passively administered to mice. This antibody binds a site on the virus E1 glycoprotein that is exposed on infected cells during virus maturation but is not exposed on virions. K42 was also found to bind to and cause cell death of, some TC-83-infected Vero cells, but does not do so with V3526-infected cells. Together these data suggest that alphavirus interference by the K42 antibody occurs at the surface of infected cells. The ability of V3526 to avoid interference is likely due to the conformational changes in its glycoprotein spikes that may sterically prevent binding of interfering antibodies.

Further, prior immunization with inactivated EEE vaccine did not interfere with subsequent responses to an influenza vaccine which was vectored in a packaged VEE virus replicon. A packaged replicon resembles a virus particle and would be susceptible to antibody-mediated inteference (clearance mechanisms) that occurs prior to cell infection. After the packaged replicon infects a cell, the influenza protein is made, but VEE virus proteins are not made. As no VEE virus structural proteins are expressed at the cell surface, replicon-infected cells will not be susceptible to interference that is mediated by cross reactive antibodies that bind sites that are exposed only on infected cells.

Therefore, it is an object of the present invention to provide a method for inducing in an alphavirus-immune recipient neutralizing antibodies against a second alphavirus comprising administering an alphavirus composition comprising said second alphavirus wherein said second alphavirus has been altered such that it is not recognized by interfering antibodies present in said alphavirus-immune recipient.

It is another object of the present invention to provide a method for providing immunity against a first alphavirus without preventing immunity from a second alphavirus comprising administering a first alphavirus vaccine wherein said alphavirus has been altered such that antibodies produced against said first alphavirus do not interfere with immunity against a second alphavirus.

It is yet another object of the present invention to provide a method for inducing in an alphavirus-immune recipient neutralizing antibodies against a Venezuelan equine encephalitis (VEE) alphavirus comprising administering a VEE composition wherein said VEE has been altered such that it is not recognized by interfering antibodies present in said alphavirus-immune recipient, such as for example, an alteration in the furin cleavage site resulting in altered glycoprotein spikes unrecognizable by interfering antibodies.

It is another object of the present invention to provide a method for eliciting immunity in a subject against a first alphavirus without preventing immunity from a second alphavirus comprising administering a first alphavirus composition wherein said alphavirus in Venezuelan equine encephalitis (VEE) which has been altered such that antibodies generated against VEE do not interfere with immunity against a second alphavirus.

BRIEF DESCRIPTION OF THE DRAWINGS

These and other features, aspects, and advantages of the present invention will become better understood with reference to the following description and appended claims, and accompanying drawings where:

FIG. 1 top, middle, and bottom show known differences between live-attenuated VEE vaccines, TC-83 (middle) and V3526 (bottom).

FIGS. 1A, 1B and 1C show known differences between live-attenuated VEE vaccines, TC-83 (1B) and V3526 (1C).

FIGS. 4A, 4B, 4C, and 4D demonstrate recognition of the cryptic epitope by K42 in a viral competitive binding assay. MAb K42 was diluted two fold starting from 0.25 ug/ml to 0.0001 ug/ml and MAb 1B4A-9 was diluted starting from 0.5 ug/ml to 0.0002 ug/ml in BSA-PBS. Each MAb dilution was equally mixed with either 1) alphavirus diluted to 50 ug/ml in PBS, 2)alphavirus incubated with 1% Triton-X-100 at room temperature for 30 minutes and diluted to 50 ug/ml, 3)PBS, or 4)PBS diluted with Triton-X-100. MAb-virus suspensions were incubated at room temperature with rocking for 30 minutes. A volume of 50 ul/well of the suspension was added to 96-well ELISA plates coated with 0.5 ug of virus per well (Fisher Scientific, Pittsburgh, Pa.) with the same virus, and prepared as described below for ELISA using CBC supplemented with 1% Triton-X-100. Plates were incubated overnight at 4° C. and developed as described for ELISA.

DETAILED DESCRIPTION

Figure 2:
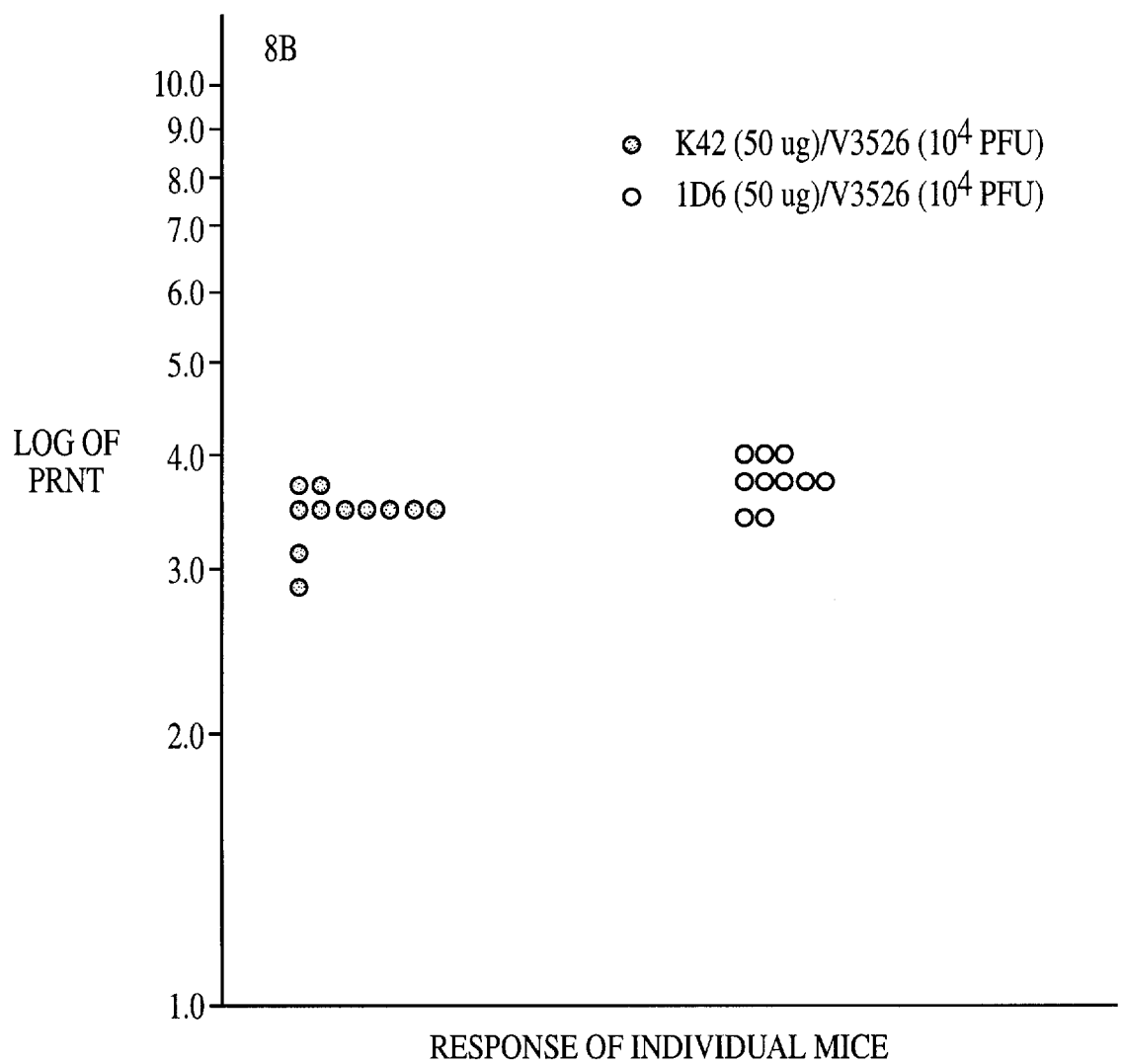
FIG. 2 shows response of individual mice to immunization with V3526 after administration of 50 ug of K42 or 1D6 (control) antibody.

In the description that follows, a number of terms used in recombinant DNA, virology and immunology are extensively utilized. In order to provide a clearer and consistent understanding of the specification and claims, including the scope to be given such terms, the following definitions are provided.

Alphaviruses. The alphaviruses are a genus within the family Togaviridae that contains 26 members, many of which are important human pathogens such as Venezuelan equine encephalitis, eastern equine encephalitis, western equine encephalitis, chikungunya, Mayaro, O'nyong-nyong, Ross River, Sindbis, to name a few. The alphaviruses are enveloped RNA-containing viruses in which an icosahedryl nucleocapsid is surrounded by a lipid-containing envelope containing two virus glycoproteins E1 and E2, present on the virus surface in hexameric spikes [Reviewed in Strauss, E. G. and Strauss, J. H. (1986) In "the Togaviridae and Flaviviridae" (S. Schlesinger and M. J. Schlesinger, Ed.), pp 35–90 Plenum, New York; Fuller, S. D. (1987) *Cell* 48: 923–934].

By "first alphavirus" is meant an alphavirus the subject is first introduced to and to which an immune reaction is mounted. By "second alphavirus" is meant a heterologous alphavirus or a different homologous virus subtype the subject is exposed to after having an immune response to the first alphavirus.

Interfering antibodies. Antibodies generated as a result of an immune reaction to a first alphavirus exposure, whether exposure is by immunization or by infection with the alphavirus. These antibodies are thought to react with a similar epitope(s) on an unaltered second alphavirus such that the immune response against said second alphavirus is compromised.

Interference. A phenomenon whereby interfering antibodies from a subject previously exposed to an alphavirus interfere with the production of an immune response in said subject to another alphavirus. Interference is defined as a three-fold reduction in the neutralizing antibody titers induced to a secondary alphavirus immunogen in the presence of prior alphavirus immunity.

An attenuated, altered alphavirus virus. Virus which has been altered, by genetic mutation for example, such that there is a decreased probability of causing disease in its host (i.e. loss of virulence), but still capable of inducing an immune reaction in an individual.

Subject. Includes both human, animal, e.g., horse, donkey, pig, mouse, hamster, monkey, chicken, and insect such as mosquito.

In one embodiment, the present invention relates to a method for overcoming interference, i.e. eliciting an immune response in an alphavirus-immune subject against a second, heterologous, alphavirus said method comprising administering to an alphavirus-immune recipient a composition comprising a live attenuated, altered second alphavirus, the alteration resulting in a change in sequence, conformation or accessibility of cross-reactive epitopes, such that interfering antibodies can no longer compromise production of an immune response against said second alphavirus.

By altered alphavirus is meant an alphavirus in which an alteration such as a genetic mutation or a recombination event or artificial change has been introduced wherein said mutation results in a change in the E1 and/or E2 glycoprotein sequence, conformation, and/or accessibility to cross-reactive epitopes. Such alterations can include the addition of a tag, or lipid [Deres et al. (1989) *Nature* 342:561–564] or the addition or change of type of sugars or addition or elimination of glycosylation sites [Strauss, E. et al. (1991) *J. Virol.* 65: 4654–4664] either through genetic manipulation or as a result of expression of the virus protein in different cell types (for example, baculovirus expression system) [Garcia-Beato, R. et al. (1996) *Virology* 221: 301–309]. The alterations can be the result of genetic mutations such as a deletion, for example, deletion of the furin cleavage site, or a substitution of an amino acid. Novel mutations can be discovered in the alphavirus by introducing deletion mutations which are not reparable by the viral RNA replication process. A preferable mutation is the deletion of the furin cleavage site between the E2 and E1 proteins. Transfection of the mutant genome into cells can cause reversion or suppression of the mutation and/or the occurance of a suppressor mutation due to the error prone process of alphavirus replication. Once efficiently replicating viral progeny is generated, they can be selected by biochemical analysis to detect the presence of PE2 protein indicating that the suppressor mutation was effective at directing synthesis of an altered viral surface glycoprotein. Introduction of mutations into cDNAs encoding live alphavirus can be by any suitable means such as site-directed mutagenesis (Please see for example, Maniatis, Fitsch and Sambrook, *Molecular Cloning: A Laboratorv Manual* (1982) or *DNA Cloning*, Volumes I and II (D. N. Glover ed., 1985) or *Current Protocols in Molecular Biology* Ausubel, F. M. et al. (Eds.) John Wiley & Sons, Inc. for general cloning methods).

In an embodiment of the invention, the second altered attenuated virus is a Venezuelan encephalitis virus (VEE), V3526 [Davis, N. L. et al. (1995) *Virology* 212: 102–110]. V3526 contains a cleavage site deletion in the PE2 glycoprotein sequence introduced using site-directed mutagenesis into a cDNA of a full length clone of VEE, and a viability restoring mutation at codon 253 of glycoprotein E1. These mutations result in an attenuated altered virion that has glycoprotein spikes containing three PE2-E1 heterodimers instead of the three E2-E1 heterodimers normally present in VEE viruses.

In another embodiment, the present invention relates to a method for providing immunity against a first alphavirus without preventing immunity from a second, heterologous alphavirus, said method comprising administering a first alphavirus vaccine comprising an live attenuated altered alphavirus such that neutralizing antibodies produced against said first alphavirus do not interfere with immunity against said second, heterologous alphavirus. Exposure to the second heterologous alphavirus can be by infection or immunization.

Vaccine formulations of the present invention comprise an immunogenic amount of a live attenuated altered virus, such as V3526 described above, or a combination of live attenuated altered viruses as a multivalent vaccine, in combination with a pharmaceutically acceptable carrier. An "immunogenic amount" is an amount of the attenuated altered virus sufficient to evoke an immune response in the subject to which the vaccine is administered. An amount of from about 10 to $10^7$ plaque forming units of the live virus per dose is suitable, depending upon the age and species of the subject being treated. Exemplary pharmaceutically acceptable carriers include, but are not limited to, sterile pyrogen-free water and sterile pyrogen-free physiological saline solution.

Administration of the live attenuated altered viruses disclosed herein may be carried out by any suitable means, including both parenteral injection (such as intraperitoneal, subcutaneous, or intramuscular injection), by in ovo injection in birds, orally and by topical application of the virus (typically carried in the pharmaceutical formulation) to an airway surface. Topical application of the virus to an airway surface can be carried out by intranasal administration (e.g. by use of dropper, swab, or inhaler which deposits a pharmaceutical formulation intranasally). Topical application of the virus to an airway surface can also be carried out by inhalation administration, such as by creating respirable particles of a pharmaceutical formulation (including both solid particles and liquid particles) containing the virus as an aerosol suspension, and then causing the subject to inhale the respirable particles. Methods and apparatus for administering respirable particles of pharmaceutical formulations are well known, and any conventional technique can be employed.

In yet another embodiment, the invention relates to a method for detecting the presence of alphavirus infection in a sample. Using standard methodology well known in the art, a diagnostic assay can be constructed by coating on a surface (i.e. a solid support) for example, a microtitration plate or a membrane (e.g. nitrocellulose membrane), all or a unique portion of K42, a monoclonal antibody directed against the structural proteins of Sindbis virus [Schmaljohn, A. L. et al. (1982) *Nature* 297:70–72; Schmaljohn A. L. et al. (1983) *Virology* 130:144–154; Stec, D. S. et al. (1986) *J. Virol.* 57: 715–720] and which binds a site (epitope) on the virus E1 glycoprotein that is exposed on infected cells during virus maturation. A sample from a subject suspected of having an alphavirus infection is brought in contact with the K42-coated plate or membrane. The presence of a resulting complex formed between K42 and its antigen specific therefor in the sample can be detected by any of the known methods common in the art, such as fluorescent antibody spectroscopy or colorimetry. This method of detection can be used, for example, for the diagnosis of alphavirus infections.

In another embodiment, the present invention relates to a diagnostic kit which contains K42 and ancillary reagents that are well known in the art and that are suitable for use in detecting the presence of alphavirus in a sample such as tissue, serum, blood. Samples contemplated can be monkey and human, or other mammals.

In another embodiment, the present invention relates to a method of reducing alphavirus infection symptoms in a patient by administering to said patient an effective amount of K42 monoclonal antibody as described above. Administration can be intradermal, intramuscular, or intravenous. When providing a patient K42 antibodies, the dosage of administered agent will vary depending upon such factors as the patient's age, weight, height, sex, general medical condition, previous medical history, etc. In general, it is desirable to provide the recipient with a dosage of the above compounds which is in the range of from about 1 pg/kg to 10 mg/kg (body weight of patient), although a lower or higher dosage may be administered.

The following MATERIALS AND METHODS were used in the examples that follow.

Animal Studies

Alphavirus naïve, 6–8 week old female BALB/c (National Cancer Institute (NCI), Ft. Detrick, Md.) were utilized for each experiment, and were identified with implantable micro identification chips (BioMedic Data System, Inc.). The following alphavirus vaccine schedule was used for all protocols unless otherwise specified.

Formalin-inactivated freeze-dried alphavirus vaccines approved for human IND status were stored at −20° C. Lyophilized inactivated C-84 vaccine (Salk Institute, Swiftwater, Pa.) containing 0.5% human serum albumin (HSA), 50 μg/ml neomycin base and 50 μg/ml streptomycin, was reconstituted in 5.5 ml of endotoxin free sterile water (Sigma, St. Louis, Mo.). Mice received 0.5 ml on days 0, 7 and 28 subcutaneously (s.c.).

Lyophilized formalin-inactivated WEE vaccine (strain CM4884) (Salk Institute, Swiftwater, Pa.) containing 50 μg/ml of neomycin, and 0.5 weight/volume (w/v) HSA was reconstituted with 5.5 ml of endotoxin free sterile water (Sigma, St. Louis, Mo.). Mice received 0.5 ml on days 0, 7, and 28 s.c.

Inactivated EEE vaccine (strain PE6 WRAIR) (Salk Institute, Swiftwater, Pa.) containing 0.25% HSA, neutralized with sodium bisulfite and 50 μg/ml neomycin was reconstituted in 3 ml of endotoxin free sterile water (Sigma, St. Louis, Mo.). Mice received 0.5 ml of vaccine s.c. on days 0 and 28.

Live-attenuated freeze-dried TC-83 (National Drug Company, PA) was stored at −20° C. The TC-83 vaccine containing 0.5% HSA, 50 μg/ml of neomycin and 50 μg/ml of streptomycin was reconstituted with 5.5 ml of endotoxin free sterile water (Sigma, St. Louis, Mo.). Each mouse received 0.5 ml [approximately $10^4$ plaque forming units (PFU)] on day 0 s.c. For dose experiments, TC-83 was passed once through BHK cells, and was diluted in Eagle's minimum essential medium/non-essential amino-acids (EMEM/NEAA). Mice were immunized s.c. with 0.5 ml of $10^3$, $10^4$, $10^5$ or $10^7$ PFU of TC-83.

The live-attenuated freeze-dried CHIK vaccine (Salk Institute, Swiftwater, Pa.) containing less than 0.02 μg of neomycin and 0.25% HSA was reconstituted in 21 ml of endotoxin free sterile water (Sigma, St. Louis, Mo.). Each mouse received 0.5 ml [approximately $10^5$ PFU] on day 0 s.c.

Transfection supernatant of the VEE vaccine candidate, V3526 was stored at −70° C. V3526 was diluted in EMEM/NEAA, and mice received 0.5 ml with approximately $10^3$, $10^4$, $10^5$, or $10^6$ PFU s.c.

The Venezuelan replicon particle (VRP) expressing hemagglutinin (VRP-HA) was provided by Dr., and Dr. Nancy Davis, UNC, and stored at −70° C. VRPs were diluted in PBS and $2 \times 10^6$ IU in 0.2 ml were administered to mice on days 40, 72 and 136. For all experiments sham-immunized mice received 0.5 ml or 0.2 ml of 0.5% HSA diluted in EMEM.

As described in Davis et al., 1995, *Virology* 212, 102–110. Briefly, a full length cDNA clone from the virulent Trinidad donkey strain of VEE, V300 (Davis et al., 1989, *Virology* 171, 189–204; Davis et al. 1991, *Virology* 183, 20–31) was used as the parent sequence. Molecularly cloned mutants were produced by a modification of the Kunkel method (Kunkel, 1985, *Proc. Natl. Acad. Sci. USA* 82, 488–492) for site-directed mutagenesis of an M13 subclone of the V3000 structural protein genes, followed by cloning of the E1 or E2 gene, or both, into a pUC118-based shuttle vector for final transfer into a full-length clone as described in Grieder et al. (1995, *Virology* 206, 994–1006). The entire region subjected to mutagenesis was checked by direct sequence analysis of RNA transcripts to ensure that only the desired mutation(s) was present. V3526 contains a deletion of the entire four-amino-acid cleavage signal (E3 56–59, Arg-Arg-Lys-Arg) immediately upstream from the PE2 cleavage site and an additional single-nucleotide change at nt 10,755 (nucleotides numbered according to Kinney et al., 1989, *Virology* 170, 19–30), resulting in a change to Ser at E1 codon 253 from the parental strain.

Blood Collection and Processing

After the primary or secondary series of each vaccine the mice were anesthetized by inhalation with Metofane (MallinckRodt Veterinary, Inc. Mundelein, Ill.) and bled from the retro-orbit al sinus. Blood was centrifuged at 1800 xg for 10 minutes, sera were collected and stored at −70° C.

Animal Challenge

Approximately 30 days after the last dose of the secondary immunization, mice received $10^4$ PFU of virulent Trinidad donkey (TrD) in 0.5 ml s.c. For VRP experiments mice were challenged intranasally (i.n.) with 20 μl infectious A/PR/8/34 (H1N1) strain of influenza at $3 \times 10^5$ egg infectious doses ($EID_{50}$) diluted in phosphate buffer saline (PBS) (40 mM NaCl, 0.75 mM KCl, 44 mM $KH_3PO_4 \cdot H_2O$, pH 7.4).

After TrD challenge, mice were observed for 30 days after challenge for sickness (i.e. ruffled fur, hunched backs) and death. Influenza challenged mice were weighed each day for 15 days after flu challenge. Sickness with influenza-challenge mice was defined as loss of 10% of the i initial body weight for 3 continuous days. Thirty days after receiving the TrD or influenza challenge, mice were bled and euthanized.

Alphavirus Production and Purification

Baby hamster kidney (BHK) cells were grown to confluence in 850 cm²/roller bottles. Complete EMEM [EMEM supplemented with 25% fetal bovine serum (FBS), 5% hepes buffer solution (1 M) (Gibco BRL, Life Technologies, Grand Island, N.Y.), 5 U/ml penicillin and 5 μg/ml streptomycin (Gibco BRL, Life Technologies, Grand Island, N.Y.) and 0.1 mg/ml gentamicin (Bio Whittaker, Walkersville, Md.)] was prepared. Alphavirus with the multiplicity of infection (MOI) of 10 per roller bottle was added to pre-warmed complete EMEM (37° C.)

After discarding the media in the roller bottles, 10 ml of virus-EMEM solution was added to each bottle. Infected roller bottles were stored with continuous rolling at 37° C. for 60 minutes. Complete EMEM (40 ml) was added to each roller bottle, and incubated at 37° C. for 12–20 hours until 50–85% cytopathic effects were observed. The contents of the roller bottles were decanted and spun at 10,000 ×g in a GSA rotor for 30 minutes at room temperature. Supernatants were poured over a mixture of polyethylene glycol (PEG) solution (7% polyethylene glycol and 2.3% NaCl weight/volume) and stirred at 4° C. overnight. The PEG-solution was removed and spun at 10,000 ×g in a GSA rotor for 30 minutes at room temperature. The pellets were suspended in 10 ml sterile PBS, and then gently pipetted over a 20–60% sucrose gradient: 15 ml of 20% sucrose: [100 g sucrose and 400 ml Hank's Balanced Salt Solution (HBSS)] and 15 ml of 60% sucrose [300 g sucrose, 200 ml HESS] mixed via a densi-flow machine (Buchler Instruments Division, Chicago, Ill.). The gradient was spun on a Beckman L8-55 ultracentrifuge in a swing (SW28) rotor at 110,000 ×g for 3.5 hours at 4° C. The virus band was collected, aliquoted and stored at −70° C.

Monoclonal Antibodies

Mice received sequential immunizations of TC-83 (day 0), TrD (day 42), EEE (day 70), WEE vaccine (day 98), and CHIK vaccine (day 126). A month after the last vaccination, they were bled and their sera were screened by ELISAs for EEE and WEE antibodies. Two mice with the highest serum titer concentrations to both antigens were identified and received 40 $\mu$g/ml of irradiated TC-83 (8 million radioactive units) intravenously. After three days, the mice were killed by cervical dislocation, and their spleens were aseptically removed. MAbs for this project were produced by Shawn Guest (USAMRIID) as described in Stiles et al. (1991) [*Toxicon* 29: 1195–1204].

Hybridoma supernatants were screened by ELISA for binding to CHIK and Sindbis virus coated plates. Cells producing antibodies that bound to both viruses were identified and cloned twice. Hybridoma cells producing MAb of interest 6F10 were grown in hybridoma serum-free medium 1× (Gibco BRL, Grand Island, N.Y.) in cell culture or in a Cell-Pharm 100 hollow fiber system (Unisyn Technologies, CA) to produce a sufficient stock of MAb.

Protein A purified monoclonal antibody (MAb) K42 was generously supplied by Dr. Alan Schmaljohn (USAMRIID). This MAb was prepared by initial immunization with Sindbis virus and an i.v. booster with Semliki Forest virus. It has been described as an IgG2a, anti-E1 cryptic epitope MAb which is cross-reactive on alphaviruses (Schmaljohn, A. personal communication).

The negative control 1D6 MAb was provided by cell culture division (USAMRIID) and has been described in Stiles et al. (1991). 1D6 is an anti-Streptoendotoxin-A (SEA) MAb with an IgG2a isotype. It was grown in cell culture and used as the negative control in passive transfer experiments. The positive control 1B6-9 MAb was used in the competitive binding assay and has been previously described by Roehrig et al. (1988) [*Virology* 165:66–73] as an IgG2a, anti-E1 neutralizing and protective MAb.

Enzyme Linked Immunosorbent Assay (ELISA)

Sucrose-gradient purified viruses at concentrations of 5 $\mu$g/ml of TC-83, 5 $\mu$g/ml Sindbis (SIN), 5 $\mu$g/ml V3526, 2 $\mu$g/ml of EEE, 2 $\mu$g/ml of WEE, 5 $\mu$g/ml of CHIK, and 0.07 $\mu$g/ml of influenza were prepared in carbonate bicarbonate buffer (CBC) [35 mM NaHCO$_3$, 15 mM Na$_2$CO$_3$, pH 9.6].

A volume of 50 $\mu$l/well was added to 96 well-bottom plates (Falcon 3912, Oxnord, Calif.) and incubated at 4° C. overnight. The plates were washed three times with PBS-Tween 20 (PBS supplemented with 27 mM NaN$_3$, 0.15% Tween 20) and blocked with 100 $\mu$l/well of bovine serum albumin (BSA-PBS) blocking buffer (Kirkegaard and Perry Laboratories (KPL), Gaithersburg, Md.) at 37° C. for one hour, frozen at −20° C. and washed with PBS-Tween before use.

Serum samples were serially diluted three-fold from 1:100 to 1:656,100. Diluted serum samples (50 $\mu$l/well) were added to antigen coated plates. PBS-BSA was used as background control. K42 (1 $\mu$g/ml) was utilized to bind to alphaviruses as positive control. Diluted positive control serum from a mouse hyperimmunized to influenza was utilized for influenza plates as positive control. The plates were incubated at 37° C. for one hour, and washed with PBS-Tween. A volume of 50 $\mu$l/well of alkaline phosphatase conjugated-rabbit anti-mouse IgG gamma (KPL, Gaithersburg, Md.) diluted to 1 $\mu$g/ml in BSA-PBS was added to the plates, and incubated at 37° C. for one hour. The plates were washed as described above and 50 $\mu$l of the substrate buffer, p-nitrophenyl phosphate (Sigma Diagnostics, St. Louis, Mo.) at 1 mg/ml in substrate buffer (1 M Tris base solution supplemented with 200 $\mu$l of 1.5 M MgCl$_2$, pH 9.8) was added to each well. After 30 minutes at room temperature, the absorbance of each well was read at optical density (O.D.)$_{405}$ using an ELISA microplate reader (Dynatech MR5000). Endpoint titer was determined as the last dilution that gave a 0.25 or a 0.2 O.D. value above background on alphavirus and influenza plates respectively.

Quantitation ELISA Assay

Falcon 96-well plates were prepared as described above except using goat anti-mouse IgG-gamma antibody (KPL, Gaithersburg, Md.) at 1 $\mu$g/ml to coat the plate. MAbs or mouse polyclonal sera were used undiluted and were serially diluted two-fold in BSA-PBS to 1:20480. K42 MAb at 0.8 ng/ml was used as positive control. Plates were incubated at room temperature for 3 hours. The plate were read on an ELISA reader (molecular Devices, Sunnyvale, Calif.) using the Softmax Program (Molecular Devices), and quantitation of antibody concentrations were determined from standard curves of MAb K42.

Competitive Inhibition by Viral Antigen

MAbs were serially diluted two-fold in BSA-PBS starting from 0.25 $\mu$g/ml to 0.0001 $\mu$g/ml for K42 and 0.5 $\mu$g/ml to 0.0002 $\mu$g/ml for 1B4A-9. Each of the MAb dilutions were mixed with an equal volume (75 $\mu$l) of either 1) alphavirus diluted to 50 $\mu$g/ml in PBS, 2) alphavirus incubated with 1.0% Triton-X-100 at room temperature for 30 minutes and diluted to 50 $\mu$g/ml, 3) PBS, or 4) PBS diluted with Triton-X-100. MAb-virus suspensions were incubated at room temperature with rocking for 30 minutes. A volume of 50 $\mu$l/well of the suspension was added to 96 well antigen-coated Falcon plates, and prepared as described above for ELISA using virus denatured with 1% Triton-X. Plates were incubated overnight at 4° C. and developed as described for ELISA.

Immunofluorescence Assay (IFA)

The medium from a confluent T150 flask of BHK cells was discarded and 10 ml of sterile PBS was added to the flask. After gently swirling the flask the PBS was discarded and 3 ml of 1× trypsin-ethylenediaminetetracetic acid solution (Sigma, St. Louis, Mo.) was added. The flasks were placed horizontally at 37° C. for 2 minutes. The medium in the flasks were added to complete medium (EMEM/NEAA, 10% FBS, 100 U/ml penicillin and 100 $\mu$g/ml streptomycin and 0.1% gentamicin), and the contents were mixed gently.

Cells were counted using a hemacytometer, resuspended to $10^4$ cells/ml, and 400 μl was added to each cell chamber of LabTek slide (Nunc Inc., Napersville, Ill.), and incubated overnight at 37° C., 5% $CO_2$. The media was discarded, and 100 μl of $10^2$ IU of VRP or $10^2$ PFU of virus diluted in complete medium was added to each chamber and incubated at 37° C., 5% $CO_2$ for 1 hour. A volume of 400 μl of the complete medium pre-warmed to 37° C. was added to each chamber and the chambers were incubated overnight at 37° C., 5% $CO_2$.

The medium was discarded, and the sealing gaskets were gently removed from the slides. The slides were rinsed in PBS at room temperature with gentle mixing for 3 minutes, and allowed to completely air dry. The slides were placed in −20° C. acetone for 20 minutes, and then allowed to air dry. A volume of 200 μl of rabbit anti-VEE antibody (1:18), or mouse anti-flu antibody (1:6) diluted in PBS with 20% FBS was added to each slide. The slides were incubated in a moist chamber for 30 minutes at room temperature and rinsed with PBS for 3 minutes with gentle mixing and allowed to air dry. A volume of 200 μl of affinity purified rhodamine-labeled goat anti-mouse rabbit IgG (heavy & light chain) (KPL, Gaithersburg, Md.), or affinity purified antibody fluorescein-labeled goat anti-mouse IgG (heavy & light chain) (KPL, Gaithersburg, Md.) at 55 μg/ml and at 33 μg/ml, respectively in PBS with 20% FBS was added to each slide. The slides were incubated for 30 minutes in a moist chamber at room temperature, rinsed for seven minutes in PBS bath and allowed to air dry. One to two drops of Vectashield mounting medium (Vector Laboratories Inc., Burlingame, Calif.) along with cover slips were placed on the slides. The slides were examined under a Zeiss Axioplan Epi-Fluorescence microscope (Carl Zeiss Inc., West Germany).

Western Blot

A 13% acrylamide N,N'Diallytartardiamide (DATD) resolving gel was prepared in a transfer electrophoresis series electrophoresis cell apparatus (Hoeffer, San Francisco, Calif.). A 5% stacking gel was prepared and added above the resolving gel. The apparatus was placed in a chamber with electrode buffer (0.76 M Glycine, 0.01 M Tris, 0.01 M sodium-dodecyl sulfate (SDS)). Pre-stained markers (Bio-Rad, Richmond, Calif.), or purified alphavirus at 1 μg/ml were loaded into wells. The proteins were electrophoresed at 70 volts overnight.

The sodium-dodecyl sulfate polyacrylamide (SDS-PAGE) gel was removed from the gel apparatus and soaked in 1× transfer buffer (20 mM Tris, 2 M Glycine) for 5 minutes. Nitrocellulose membrane (0.45 μm) (Schleicher & Schuell, Opittran BA-S reinforced nitrocellulose) was pre-soaked in transfer buffer and the gel was placed between the nitrocellulose membranes. Using a Hoeffer electroblot transfer tank, the gel was electroblotted at 12° C. at 0.4–0.5 Amperes. After 2 hours, the nitrocellulose was blocked with 5% skim milk at room temperature, and cut into strips. MAbs or hyperimmune mouse ascitic fluid (HMAF) to TC-83 (ATCC, Rockville, Md.) were diluted 1:100 or 1:1000 in 5% skim milk and 5 ml of each was incubated with the strips at room temperature for 1 hour with gentle rocking. The strips were then washed three times with deionized water followed by a 5 minute wash with Tris buffered solution (50 mM Tris-HCl, 0.2 M NaCl, pH 7.4). A volume of 5 ml of horse-radish peroxidase labeled anti-mouse IgG (Amersham Life Sciences, England, Catalog # NA931) at 1:1500 in 5% skim milk was added to the strips, and incubated 1 hour at room temperature. The blots were washed as described above. To develop by enhanced chemiluminescence (ECL), the nitrocellulose strips were soaked in color developer (Amersham Life Sciences, England). The blot was exposed to Kodak BIOMAX film for 10 minutes or less, and an x-ray film was developed.

MAb Passive Transfer

MAbs K42, 6F10 or negative control 1D6 were diluted in hybridoma serum-free medium 1× (Gibco BRL, Grand Island, N.Y.). Each mouse received 50 or 100 μg of the MAbs intraperitoneally (i.p.) on day one. The mice were bled on day 2, and 5 hours later mice received either $10^4$ PFU of TC-83, V3526 or TrD virus. Control mice received serum free medium i.p. Animals were observed for 30 days for any clinical signs of sickness or death. Animals were bled at 2, 4, and 6 weeks post infection. Sera were collected and screened by ELISA and PRNT. At 7 weeks mice received $10^4$ PFU/mouse of TrD s.c. and were observed for 30 days for clinical signs of sickness or death.

Polyclonal Passive Transfer

Mice received the EEE or WEE vaccine series or 0.5% HSA diluted in EBME. The mice were bled 35 days after the first dose of the vaccines, killed and their sera pooled and evaluated by ELISA and PRNT titers for EEE or WEE viruses.

Naive mice received 1 ml of the mouse polyclonal sera to EEE, WEE or HSA i.p. The following day the mice were bled and 5 hours later each mouse received the TC-83 vaccine or 0.5% HSA. Mice were bled 2, 4 and 6 weeks post immunization. Sera were screened for EEE, WEE and VEE neutralizing antibodies using PRNT.

Quantitative Plaque Assay

The titers of all viral immunizations were determined by preparing serial 10 fold dilution of the virus immunogen in HBSS, 2% FBS and 0.02 U/ml penicillin and 0.02 μg/ml streptomycin. The medium of confluent Vero cells were decanted and infected with 0.1 ml of virus per well, and incubated at 37° C. with gentle rocking every 15 minutes. At one hour post infection, the wells were overlaid with 2 ml of overlay (EBME supplemented with 20% FBS, 0.2 mM non-essential amino acids, 0.1 mg/ml gentamicin, 400 U/ml penicillin and 400 ug/ml streptomycin, 4 mM L-glutamine and 0.6% of agarose pre-warmed to 41° C.). The plates were incubated overnight at 37° C., 5% $CO_2$. The following day, 2 ml of the second overlay (day one overlay supplemented with 0.7% of agarose and 5% neutral red solution (Gibco BRL Life Technologies, Grand Island, N.Y.) was added to each well. The plates were incubated overnight at 37° C., 5% $CO_2$, and the number of PFU in each well were recorded.

Plague Reduction Neutralization Test (PRNT)

Each serum sample was inactivated at 56° C. for 30 minutes and serially diluted two-fold from 1:20 to 51:40960 in HBSS, 2% FBS (inactivated at 56° C. for 30 minutes), 10 U/ml penicillin and 10 μg/ml streptomycin. An equal volume (125 μl) of alphavirus (VEE IA/B V3000, EEE PE6, WEE CBA, and CHIK 181 strain) at $2\times10^3$ PFU/ml was added to diluted serum or virus-specific HMAF and incubated overnight at 4° C. The following day, confluent Vero cells were infected as described in the quantitative plaque assay and stained with neutral red as described above. Endpoint neutralization titers were based on initial serum dilutions that resulted in an 80% reduction in the number of plaques observed in the control plates. EEE and WEE virus PRNTs were generously tested by Cathy Lind (USAMRIID).

Bicinchoninic Acid (BCA) Protein Assay

BSA standards (Pierce, Rockford, Ill.) of 0 μg/ml, 200 μg/ml, 400 μg/ml, 800 μg/ml, 1200 μg/ml, 1600 μg/ml, 1800 μg/ml and 2000 μg/ml in sterile PBS were prepared. Sucrose gradient purified virus was diluted 10 fold in PBS. A volume of 10 μl of prepared standards, and 10 μl of the diluted virus were added to separate duplicate wells on a 96 well plate (Costar Cambridge, Mass.). Bicinchoninic acid (BCA)-assay reagents A and B (Pierce, Rockford, Ill.) were prepared in a ratio of 50:1, and 200 μl of the mixture was added to each well. The plate was incubated at 37° C. for 30 minutes. Absorbance was read at 405 nm, and O. D. values were plotted on Table Curve 2D program (Jandel Scientific) to determine protein concentrations.

Ab-dependent Complement-mediated Cytotoxicity (ADCMC)

T-75 flasks of confluent VERO cells were infected with virus at an MOI of 1 and incubated for 14 hours at 37° C. in a 5% $CO_2$ atmosphere (Schmaljohn, et al. 1983). Cells were briefly rinsed 2 times with 2 ml of trypsin (1x, Cat. # T3924, Sigma), then incubated with 2 ml trypsin for 5 minutes at 37° C. in a 5% $CO_2$ atmosphere.

Cells were washed with EMEM-5% FBS and centrifuged at 200 × g for 5 minutes. Cells were washed again with serum-free EMEM and labeled with 150 uCi of $^{51}Cr$ (185 mBq, Dupont, Boston, Mass.) in 1 ml of serum-free EMEM for 1 hour at 37° C. in a 5% $CO_2$ atmosphere. Cells were washed again with EMEM-5% FBS, and 0.1 ml containing $4 \times 10^4$ cells/ml was seeded per well into 96-well sterile cell culture plates. Guinea pig complement (Cedarlane, Canada) was added at a final concentration of 5% (v/v). MAbs including the isotype-matched negative controls and the positive control, were serially diluted 3-fold from 10 ug/ml and then added (0.05 ml/well) to triplicate wells. Triton X-100 was added to 6 wells at a final concentration of 1% (v/v) to determine maximum release and medium alone was added to another 6 wells to determine spontaneous release. Spontaneous release did not exceed 14% of maximum release for any virus. Uninfected cells were used as a negative control.

Plates were incubated 3.5 hours at 37° C. in a 5% $CO_2$ atmosphere. Supernatant (0.1 ml) was then removed from each well and counted on a Beckman gamma 5500 counter (Beckman, Fullerton, Calif.) The percent specific $^{51}Cr$ release was calculated: % specific release=Test cpm (sample)−control cpm (media)×100 divided by Maximum releasable cpm (1% Trion X)−control cpm. [Schmaljohn, et al. 1983].

EXAMPLE 1

Model of Interference

A murine model of interference was established by using BALB/c mice to study alphavirus vaccines. The availability of murine-specific reagents allowed better characterization of the immune responses mediating interference. "Checkerboard" style experiments were prepared in which the alphavirus vaccines for VEE, EEE, WEE and CHIK viruses were tested for the capability to induce immune responses that interfered with the development of neutralizing antibodies to a second alphavirus vaccine. Mice were immunized with one vaccine, and bled (indicated as post primary). The animals were then immunized with a second vaccine approximately four weeks later, and bled after the completion of the secondary vaccination series (indicated as post secondary). Sera were evaluated by ELISA and PRNT.

Sera obtained from mice after the primary EEE, WEE or VEE vaccine series demonstrated cross-reactive binding to EEE, WEE and VEE by ELISA (Table 2A, B, C). In addition, a lack of cross-reactive neutralization between EEE, WEE and VEE alphaviruses was observed by PRNT (Table 3A, B, C). Cross-reactivity in ELISA (Table 2D) but not PRNT (Table 3D) was also observed between CHIK and VEE viruses. Geometric mean titers (GMTs) of <100 in ELISA and <20 in PRNT indicated that samples were negative in the assay. Because of alphaviruses' lack of crossreactivity by PRNT, post secondary titers were established as the criterion to evaluate interference. Post secondary PRNT titers of mice that were sham-immunized during the primary series were compared to titers of mice with pre-existing alphavirus immunity. PRNT GMTs that were at least three-fold less than control GMTs were tested for statistical significance by the Student's t- test using Statistical Analysis System (SAS) version 6.10 (Cary, N.C.). A P value of >0.05 indicated no statistical significance between the control and the experimental groups.

EXAMPLE 2

Formalin-inactivated vaccines as Secondary Immunogens

The formalin-inactivated vaccines for EEE and WEE viruses were used as secondary immunogens in mice previously immunized with the VEE vaccines C-84 or TC-83. Since not all inbred mice in this experiment responded to the TC-83 vaccine, only mice that made antibodies to the primary TC-83 vaccine by ELISA were evaluated. Although cross-reactive ELISA titers (Table 3A) were present, no reduction in EEE or WEE PRNT titers were observed in TC-83 or C-84 immune mice (P>0.05) (Table 3A, B). Similarly, administration of the C-84 formalin-inactivated vaccine in mice previously immunized with EEE, WEE or CHIK vaccines resulted in no reduction of VEE PRNT titers compared to sham-immunized mice (P>0.05) (Table 3C, E).

Administration of C-84 as the secondary immunogen after EEE, WEE or CHIK vaccination induced protective immunity upon virulent TrD challenge in all tested mice (Table 3C, E). EEE or WEE immunity alone also mediated crossprotection to virulent TrD in some mice (Table 3A, B, C, D).

EXAMPLE 3

Live-attenuated TC-83 as Secondary Immunogen

Subcutaneous immunization of mice with the live-attenuated TC-83 vaccine as the secondary immunogen in the presence of prior immunity to EEE or CHIK resulted in a significant reduction in secondary VEE PRNT titers (P<0.05) (Table 3C experiment 1 and 2, Table 3E). No significant VEE PRNT reduction was measured in the presence of WEE immune mice (P=0.09) (Table 3C, experiment 1), and more WEE/TC-83 immunized animals tended to survive TrD challenge than WEE/medium control immune mice.

TABLE 2

Evaluation of Murine Antibody Responses to Primary and Secondary Alphavirus Vaccines

| primary/secondary | n[b] | ELISA IgG (GMT)[c] POST PRIMARY ELISA EEE | VEE | WEE | POST SECONDARY ELISA EEE | VEE | WEE |
|---|---|---|---|---|---|---|---|
| A. VEE THEN EEE OR WEE Immunogens[a] | | | | | | | |
| medium/EEE | 10 | <100 | <100 | <100 | 52000 | 1700 | 3750 |
| C-84/EEE | 10 | 2400 | 90000 | 60 | 33800 | 47000 | 7260 |
| TC-83/EEE | 5 | 2700 | 379000 | 2170 | 272000 | 101300 | 580 |
| medium/WEE | 10 | <100 | <100 | <100 | 2200 | 270 | 47000 |
| C-84/WEE | 10 | 3000 | 42000 | 2700 | 3750 | 17500 | 3400 |
| TC-83/WEE | 5 | 5220 | 527000 | 3360 | 10090 | 91000 | 72900 |
| C-84/medium | 10 | 3360 | 47000 | 2170 | 4670 | 15700 | 1740 |
| TC-83/medium | 10 | 6500 | 732000 | 3750 | 9040 | 65320 | 5830 |

| primary/secondary | n | ELISA IgG (GMT)[b] POST PRIMARY ELISA EEE | VEE | WEE | POST SECONDARY ELISA EEE | VEE | WEE |
|---|---|---|---|---|---|---|---|
| B. EEE OR WEE THEN VEE Immunogens[a] | | | | | | | |
| medium/C-84 | 10 | <100 | <100 | <100 | 3750 | 72900 | 2420 |
| EEE/C-84 | 10 | 38000 | 1400 | 420 | 244000 | 24300 | 170 |
| WEE/C-84 | 10 | 1560 | 3700 | 12570 | 10090 | 37800 | 37800 |
| medium/TC-83 | 8 | <100 | <100 | <100 | 5210 | 580000 | 1250 |
| EEE/TC-83 | 10 | 38000 | 1700 | 1250 | 58000 | 6500 | 2700 |
| WEE/TC-83 | 10 | 900 | 2400 | 10090 | 7260 | 58000 | 175000 |
| EEE/medium | 10 | 81400 | 1600 | 2170 | 72900 | 580 | 1400 |
| WEE/medium | 10 | 1740 | 2200 | 6500 | 2700 | 420 | 196000 |

| primary/secondary | n | ELISA IgG (GMT)[b] POST PRIMARY ELISA EEE | VEE | WEE | POST SECONDARY ELISA EEE | VEE | WEE |
|---|---|---|---|---|---|---|---|
| C. V3526 VACCINE CANDIDATE Immunogens[a] | | | | | | | |
| medium/EEE | 10 | <100 | <100 | <100 | 52000 | 1700 | 3750 |
| V3526/EEE | 9 | 17000 | 1415000 | 5830 | 196000 | 1020000 | 30270 |
| medium/WEE | 10 | <100 | <100 | <100 | 2200 | 270 | 47000 |
| V3526/WEE | 10 | 11260 | 1415000 | 5830 | 52430 | 5900000 | 113000 |
| V3526/medium | 9 | 15660 | 656100 | 5220 | 12570 | 3050000 | 15660 |
| medium/V3526 | 9 | <100 | <100 | <100 | 13200 | 224000 | 5620 |
| EEE/V3526 | 10 | 47000 | 520 | 1000 | 334000 | 5900000 | 4680 |
| WEE/V3526 | 10 | 1250 | 1600 | 91000 | 14030 | 1270000 | 101000 |

| primary/secondary | n | ELISA IgG (GMT)[b] POST PRIMARY CHIK | VEE | POST SECONDARY CHIK | VEE |
|---|---|---|---|---|---|
| D. CHIK THEN VEE Immunogen[a] | | | | | |
| medium/TC-83 | 8 | <100 | <100 | 520 | 12560 |
| CHIK/TC-83 | 10 | 5220 | 190 | 3760 | 3000 |
| CHIK/C-84 | 10 | 3360 | 220 | 4190 | 6500 |
| medium/C-84 | 10 | <100 | <100 | 270 | 2420 |
| CHIK/V3526 | 10 | 900 | 110 | 2170 | 21770 |
| medium/V3526 | 9 | <100 | <100 | 1020 | 31020 |
| CHIK/medium | 10 | 3050 | 120 | 3360 | 190 |

TABLE 2-continued

Evaluation of Murine Antibody Responses to Primary and Secondary Alphavirus Vaccines

[a]Mice received 0.5 ml with $10^4$ live-attenuated TC-83, $10^4$ live-attenuated V3526 or 0.5% HSA as medium on day 0. Formalin-inactivated C-84 vaccine (0.5 ml) was given s.c. on days 0, 7 and 28. EEE and WEE vaccines (0.5 ml) were given s.c. on days 0, 28 and 0, 7, 28 respectively. Mice received 0.5 ml of live-attenuated CHIK vaccine on day 0 and day 53.
[b]Number of mice tested.
[c]Mice were bled on day 35 after the primary and on day 77 after the completion of the secondary series. The geometric mean endpoint titers (GMTs) have been noted.

TABLE 3

Evaluation of Interference with the Induction of Heterologous Neutralizing Antibody Responses to Alphavirus Vaccines in BALB/c Mice

| Immunogens[a] | POST PRIMARY PRNT | | | POST SECONDARY PRNT | | | P[d] | Challenge |
|---|---|---|---|---|---|---|---|---|
| primary/secondary | EEE | VEE | WEE | EEE | VEE | WEE | | survival[e] |
| A. VEE THEN EEE OR WEE | | | | | | | | |
| medium/EEE | <20 | <20 | <20 | 420 | <20 | <20 | | 5/10 |
| C-84/EEE | <20 | 1110 | <20 | 300 | 910 | <20 | | 10/10 |
| TC-83/EEE | <20 | 4460 | <20 | 540 | 8910 | <20 | | 5/5 |
| medium/WEE | <20 | <20 | <20 | <20 | <20 | 60 | | 3/10 |
| C-84/WEE | <20 | 740 | <20 | <20 | 420 | 30 | | 10/10 |
| TC-83/WEE | <20 | 2940 | <20 | <20 | 1940 | 60 | | 5/5 |
| C-84/medium | <20 | 790 | <20 | <20 | 1200 | <20 | | 10/10 |
| TC-83/medium | <20 | 2740 | <20 | <20 | 7760 | <20 | | 10/10 |

| Immunogens[a] | POST PRIMARY PRNT | | | POST SECONDARY PRNT | | | P[d] | Challenge |
|---|---|---|---|---|---|---|---|---|
| primary/secondary | EEE | VEE | WEE | EEE | VEE | WEE | | survival[e] |
| B. TC-83 THEN EEE | | | | | | | | |
| medium/EEE | <20 | <20 | <20 | 240 | <20 | <20 | | 4/5 |
| TC-83/EEE | <20 | 3620 | <20 | 110 | 7240 | <20 | | 9/10 |
| TC-83/medium | <20 | 5870 | <20 | <20 | 6760 | <20 | | 10/10 |

| Immunogens[a] | POST PRIMARY PRNT | | | POST SECONDARY PRNT | | | P[d] | Challenge |
|---|---|---|---|---|---|---|---|---|
| primary/secondary | EEE | VEE | WEE | EEE | VEE | WEE | | survival[e] |
| C. EEE OR WEE THEN VEE | | | | | | | | |
| Experiment 1 | | | | | | | | |
| medium/C-84 | <20 | <20 | <20 | <20 | 260 | <20 | | 10/10 |
| EEE/C-84 | 690 | <20 | <20 | 600 | 180 | <20 | | 10/10 |
| WEE/C-84 | <20 | <20 | 80 | <20 | 210 | 60 | | 10/10 |
| medium/TC-83 | <20 | <20 | <20 | <20 | 910(9/10) | <20 | | 8/8 |
| EEE/TC-83 | 340 | <20 | <20 | 790 | 20(1/10) | <20 | <0.0001 | 7/10 |
| WEE/TC-83 | <20 | <20 | 40 | <20 | 2560 | 150 | | 9/10 |
| EEE/medium | 400 | <20 | <20 | 840 | <20 | <20 | | 6/10 |
| WEE/medium | <20 | <20 | 30 | <20 | <20 | 100 | | 3/10 |
| Experiment 2 | | | | | | | | |
| medium/TC-83 | <20 | <20 | <20 | <20 | 2990(8/9) | <20 | | 8/9 |
| EEE/TC-83 | 440 | <20 | <20 | 470 | 320 (8/9) | <20 | 0.041 | 8/9 |
| EEE/medium | 320 | <20 | <20 | 240 | <20 | <20 | | 4/5 |

| Immunogens[a] | POST PRIMARY PRNT | | | POST SECONDARY PRNT | | | P[d] | Challenge |
|---|---|---|---|---|---|---|---|---|
| primary/secondary | EEE | VEE | WEE | EEE | VEE | WEE | | survival[e] |

TABLE 3-continued

Evaluation of Interference with the Induction of Heterologous Neutralizing Antibody
Responses to Alphavirus Vaccines in BALB/c Mice

D. V3526 VACCINE CANDIDATE

| | | | | | | | |
|---|---|---|---|---|---|---|---|
| Experiment 1 | | | | | | | |
| medium/EEE | <20 | <20 | <20 | 420 | <20 | <20 | 5/10 |
| V3526/EEE | <20 | 6300 | <20 | 740 | 8320 | <20 | 9/9 |
| medium/WEE | <20 | <20 | <20 | <20 | <20 | 60 | 3/10 |
| V3526/WEE | <20 | 3620 | <20 | <20 | 5490 | 30 | 10/10 |
| medium/V3526 | <20 | <20 | <20 | <20 | 6970 | <20 | 9/9 |
| EEE/V3526 | 280 | <20 | <20 | 970 | 9550 | <20 | 10/10 |
| WEE/V3526 | <20 | <20 | 40 | <20 | 6760 | 70 | 10/10 |
| V3526/medium | <20 | 5480 | <20 | <20 | 7240 | <20 | 9/9 |
| Experiment 2 | | | | | | | |
| medium/EEE | <20 | <20 | <20 | 170 | <20 | <20 | 4/10 |
| V3526/EEE | <20 | 2740 | <20 | 100 | 3880 | <20 | 10/10 |
| medium/WEE | <20 | <20 | <20 | <20 | <20 | 10 | 3/10 |
| V3526/WEE | <20 | 2560 | <20 | <20 | 3150 | 10 | 10/10 |
| V3526/medium | <20 | 3620 | <20 | <20 | 9550 | <20 | 10/10 |

| Immunogens[a] | PRNT (GMT)[b] | | | | | Challenge |
|---|---|---|---|---|---|---|
| | POST PRIMARY | | POST SECONDARY | | | |
| primary/secondary | CHIK | VEE | CHIK | VEE | P[d] | survival[e] |
| E. CHIK THEN VEE | | | | | | |
| medium/TC-83 | <20 | <20 | <20 | 910 (9/10) | | 8/8 |
| CHIK/TC-83 | 90 (8/10) | <20 | 120 (8/10) | 50 (4/10) | 0.0005 | 7/10 |
| medium/C-84 | <20 | <20 | <20 | 260 | | 9/9 |
| CHIK/C-84 | 150 (9/10) | <20 | 100 (8/10) | 300 | | 10/10 |
| medium/V3526 | <20 | <20 | <20 | 6970 | | 10/10 |
| CHIK/V3526 | 20 (5/10) | <20 | 60 (5/10) | 3620 | | 10/10 |
| CHIK/medium | 110 | <20 | 20 (6/10) | <20 | | 4/10 |

[a]Mice were immunized with 0.5 ml of $10^4$ live-attenuated TC-83, $10^4$ live-attenuated V3526 or 0.5% HSA as medium on day 0. Formalin-inactivated C-84 vaccine (0.5 ml) was given s.c. on days 0, 7 and 28. EEE and WEE vaccines (0.5 ml) were given s.c. on days 0, 28 and 0, 7, 28 respectively. Mice received 0.5 ml of live-attenuated CHIK vaccine on day 0 and day 53.

[b]Mice were bled on day 35 after the primary and on day 77 after the completion of the secondary series. Sera were tested for the ability to inhibit plaque formation by 80% in PRNT. GMTs are shown for each group.

[c]All mice that had received the CHIK vaccine post primary had CHIK ELISA titers.

[d]Significant statistical P values based on secondary VEE PRNTs reduced at least three-fold from controls have been noted.

[e]On day 84, mice were challenged with approximately $10^4$ PFU of TrD. Mice were monitored for sickness and death. Values indicate number of mice survived/mice tested.

EXAMPLE 4

Vaccine candidate V3526 as Primary and Secondary Immunogen

When EEE or WEE vaccines were given as the secondary immunogen in V3526 immunized mice no reduction in heterologous PRNTs were observed ($P \geqq 0.05$) (Table 3D). PRNT data initially indicated that when V3526 was administered as the secondary immunogen in the presence of EEE, WEE or CHIK immune mice, secondary VEE PRNT responses were not reduced (Table 3D, E). Subsequent experiments indicated a slight reduction in PRNT GMT of secondary V3526 in EEE and CHIK immune mice. In addition, V3526 immunized mice survived TrD. challenge whether they had received the vaccine as the primary or as the secondary immunogen in the presence of prior alphavirus immunity (Table 3D, E).

EXAMPLE 5

Evaluation of the dose Effect of Secondary TC-83 or V3526 Immunogen on Interference The dose of the secondary live-attenuated VEE vaccines administered s.c. to EEE immune mice was changed to determine whether interference could be overcome. TC-83 doses of $10^3$, $10^4$, $10^5$, $10^6$ or $10^7$ PFU were given s.c. to mice previously immunized with EEE vaccine or medium. At all tested doses of TC-83, a significant reduction in secondary VEE PRNT titers was observed ($P<0.05$) (Table 4 experiment 1 and 2). At $10^4$ PFU or higher mice survived TrD challenge (Table 4).

TABLE 4

Evaluation of Interference with the Induction of Murine Neutralization Antibodies Induced by Different Doses of TC-83 in EEE Immune BALB/c Mice

| Immunogens[a] | PRNT (GMT)[b] | | | | |
|---|---|---|---|---|---|
| primary/secondary | POST PRIMARY PRNT | POST SECONDARY PRNT | | | |
| (PFU/mouse) | EEE | EEE | VEE | P[d] | Challenge survival[c] |
| Experiment 1 | | | | | |
| EEE/TC-83 ($10^5$) | 90 | 130 | 280 (9/10) | <0.001 | 10/10 |
| EEE/TC-83 ($10^4$) | 160 | 340 | 450 (8/10) | 0.009 | 10/10 |
| EEE/TC-83 ($10^3$) | 80 | 130 | 100 (6/10) | 0.038 | 9/10 |
| medium/TC-83 ($10^5$) | <20 | <20 | 6300 | | 10/10 |
| medium/TC-83 ($10^4$) | <20 | <20 | 9550 | | 9/10 |
| medium/TC-83 ($10^3$) | <20 | <20 | 1470 (8/10) | | 8/10 |
| medium/medium | <20 | <20 | <20 | | 0/10 |
| EEE/medium | 170 | 110 | <20 | | 8/10 |
| Experiment 2 | | | | | |
| EEE/TC-83 ($10^7$) | 320 | 120 | 160 (8/10) | 0.0001 | 10/10 |
| EEE/TC-83 ($10^6$) | 230 | 130 | 100 (8/10) | <0.001 | 10/10 |
| EEE/TC-83 ($10^5$) | 690 | 300 | 70 (5/10) | 0.002 | 10/10 |
| EEE-TC-83 ($10^4$) | 640 | 260 | 20 (2/10) | 0.0003 | 10/10 |
| medium/TC-83 ($10^7$) | <20 | <20 | 5490 | | 10/10 |
| medium/TC-83 ($10^6$) | <20 | <20 | 5490 | | 10/10 |
| medium/TC-83 ($10^5$) | <20 | <20 | 5120 | | 10/10 |
| medium/TC-83 ($10^4$) | <20 | <20 | 1370 | | 9/10 |
| medium/medium | <20 | <20 | <20 | | 0/10 |
| EEE/medium | 210 | 300 | <20 | | 7/10 |

[a]Medium (0.5% HSA) or EEE inactivated vaccine was administered s.c. on days 0 and 28. TC-83 doses at approximately $10^3$, $10^4$, $10^5$, $10^6$ or $10^7$ PFU were administered on day 63.
[b]Mice were bled on day 35 and on day 70. Sera were tested for PRNT. Numbers to the right of the titers indicate number of mice that responded/total number of mice tested if less than 10/10. Serum samples from the post primary bleed were screened on heterologous antigen, and were not cross-reactive (data not shown).
[c]Statistical P values based on secondary VEE PRNTS from controls of each group have been noted.
[d]On day 77, mice were challenged with $10^4$ PFU of TrD/mouse. Values indicate the number of mice that survived/mice tested.

The apparent ability of V3526 to bypass interference in EEE immune mice was compared to TC-83 at doses of $10^3$, $10^4$, $10^5$, $10^6$ PFU. In experiment 1 (Table 5) at $10^3$ PFU the control group contained several apparent vaccine nonresponders. At higher doses, the GMT PRNT titers to V3526 were reduced two or three fold compared to control groups. This level of reduction was generally observed in these studies and achieved statistical significance when the reduction approached three fold.

Comparison of the PRNT data from the treated mice with $10^4$ PFU of V3526 to all the control mice at this dose indicated no statistical significance between groups (n=30 P=0.07). All mice survived challenge if V3526 was administered as the primary or secondary immunogen (Table 5), except when the dose of the vaccine candidate was low ($10^3$ PFU)

EXAMPLE 6

Polyclonal Passive Transfer Study

In order to demonstrate that antibody responses were mediating the reduction in PRNT titers to the TC-83 vaccine, mouse anti-EEE or anti-WEE vaccine polyclonal sera were passively administered to mice. Transfer of EEE polyclonal sera resulted in a reduction in secondary VEE PRNT titers to TC-83 (P=0.025 at 6 weeks) (Table 6); however no significant VEE PRNT reduction to TC-83 in the presence of WEE polyclonal sera was observed (P>0.05).

EXAMPLE 7

Monoclonal Antibody Passive Transfer Studies

Mice were sequentially immunized with TC-83, EEE, WEE and CHIK vaccines to induce crossreactive MAbs. A fusion was performed using spleen cells from immune mice and P3.X63Ag8.653 myeloma cells. MAbs of interest were identified based on binding to CHIK and Sindbis virus. Two MAbs were characterized by ELISA and western blot. The first MAb, 6F10, was identified as an IgG2a which reacted with VEE capsid (data not shown) and was cross-reactive by ELISA on VEE, EEE, WEE and CHIK viruses (Table 7). The second MAb 15B5, was also identified as an IgG2a, and was cross-reactive by ELISA to VEE, EEE, WEE and CHIK viruses (Table 7). This MAb bound to the E1 glycoprotein in western blot (data not shown). 15B5 was not produced to high concentration in ascites or in culture and was not further evaluated.

Figure 3:
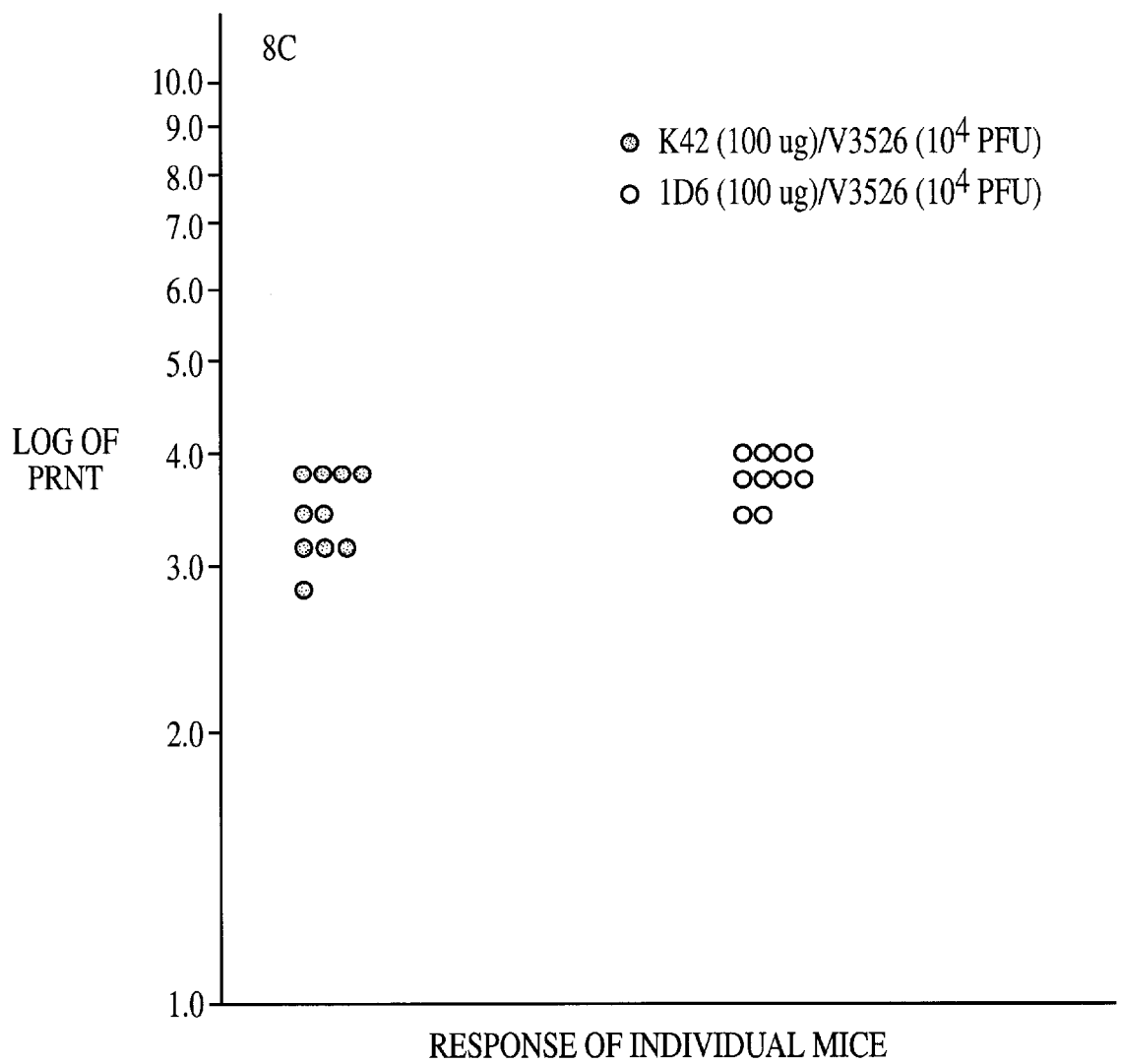
FIG. 3 shows response of individual mice to immunization with V3526 after administration of 100 ug of K42 or 1D6 (control) antibody.

MAbs 6F10, pan-alphavirus reactive MAb K42 (provided by A. Schmaljohn) and negative control MAb 1D6 were used in passive transfer experiments. Passive administration of 50 or 100 $\mu$g/mouse of MAb K42 resulted in a significant reduction in VEE PRNT titers to subsequent TC-83 immunization (P=0.001 at 6 weeks) (Table 8A, B). In similar experiments when mice were injected i.p. with 50 $\mu$g or 100 $\mu$g of K42 and then received V3526, two-fold reductions in VEE PRNT were observed at the lower doses of K42, and 3–4 fold reductions at the higher doses. FIGS. 2 and 3 illustrate the responses of individual mice compared to sham-immunized mice at 6 weeks.

No significant reduction in secondary VEE PRNT titers was observed with 6F10 (P>0.05) when the secondary immunization was TC-83 or V3526. Positive control mice that had received polyclonal EEE antisera and then TC-83 also showed a significant reduction in VEE PRNT titers (P<0.05 at 6 weeks).

At 7 weeks when mice from experiments 1 and 2 were challenged with TrD, all mice that received the secondary V3526 vaccine survived challenge. Secondary TC-83 immunization mice that induced undetectable or low PRNT titers (1:20) did not protect mice from TrD challenge.

MAbs K42 and 6F10 were also administered i.p. to mice that were challenged 24 hours later with virulent TrD to observe whether the MAbs induced any protection. K42 was partially protective at 100 μg/mouse (8/10) and less protective at 50 μg/mouse (5/20) against TrD (Table 9 experiment 1, 2, 3). Neither the control MAb 1D6 nor 6F10 protected mice from death after virulent TrD challenge (Table 9).

EXAMPLE 8

Recognition of the Cryptic Epitope

Figure 4A:
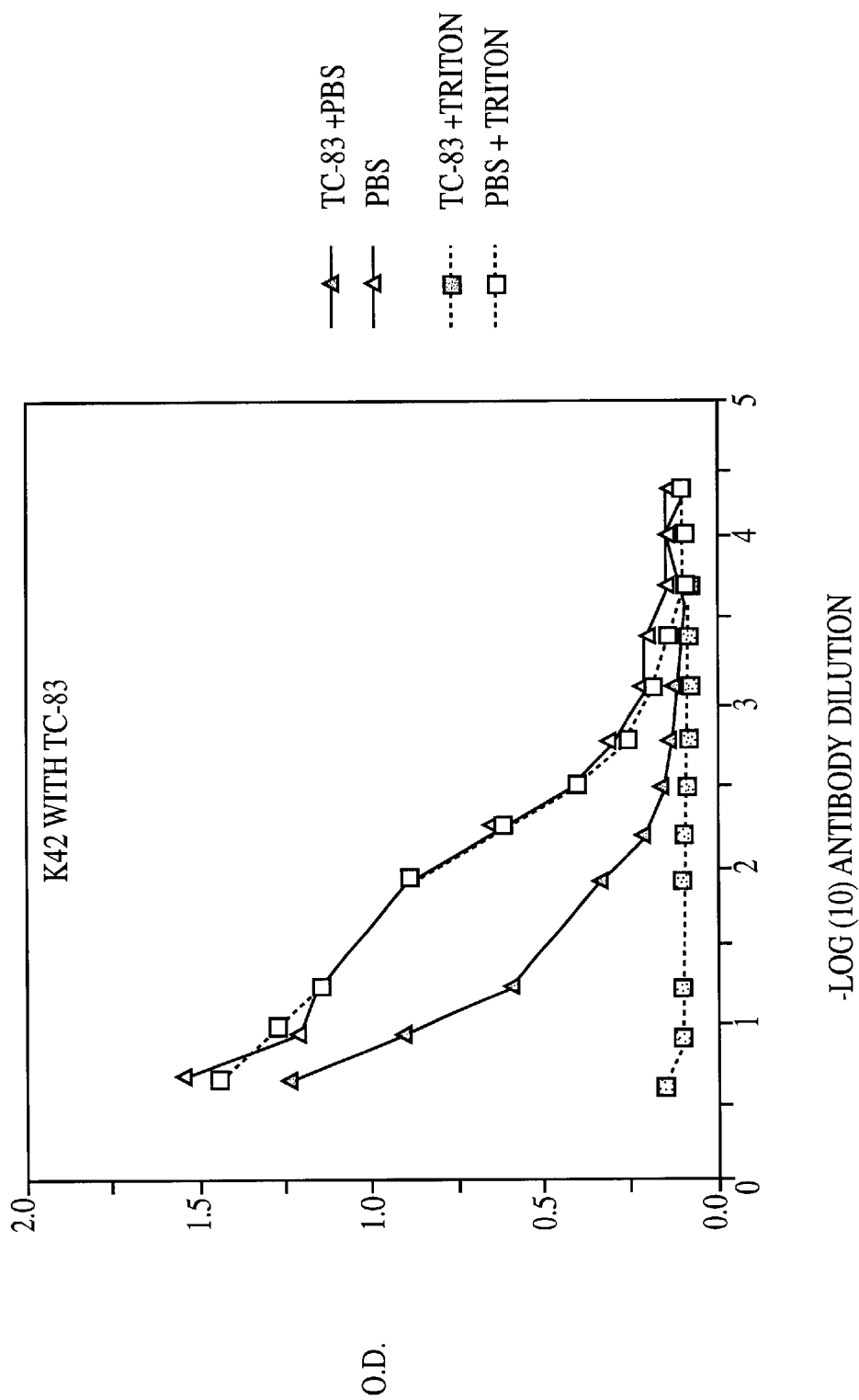
Figure 4B:
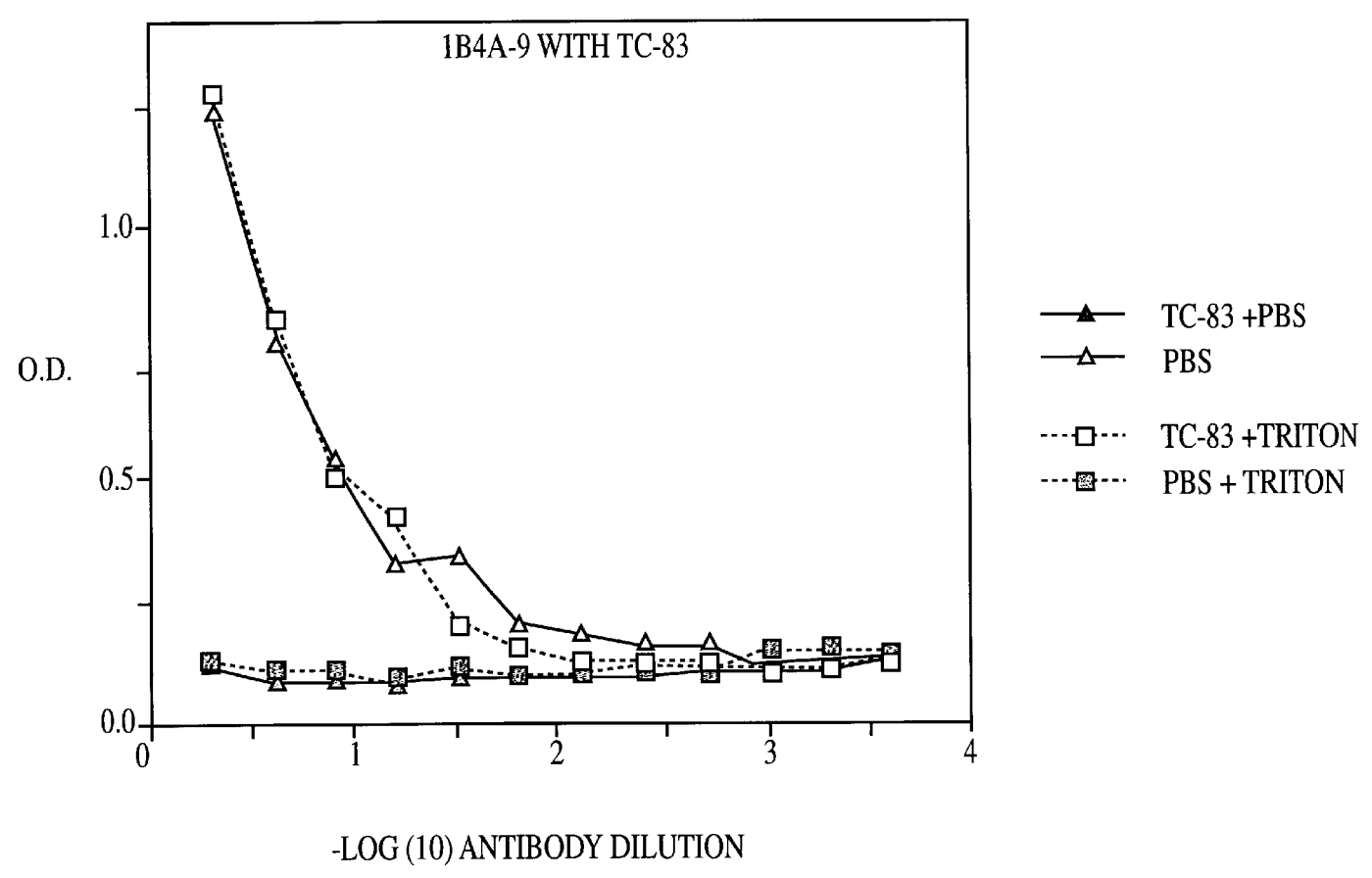
Figure 4C:
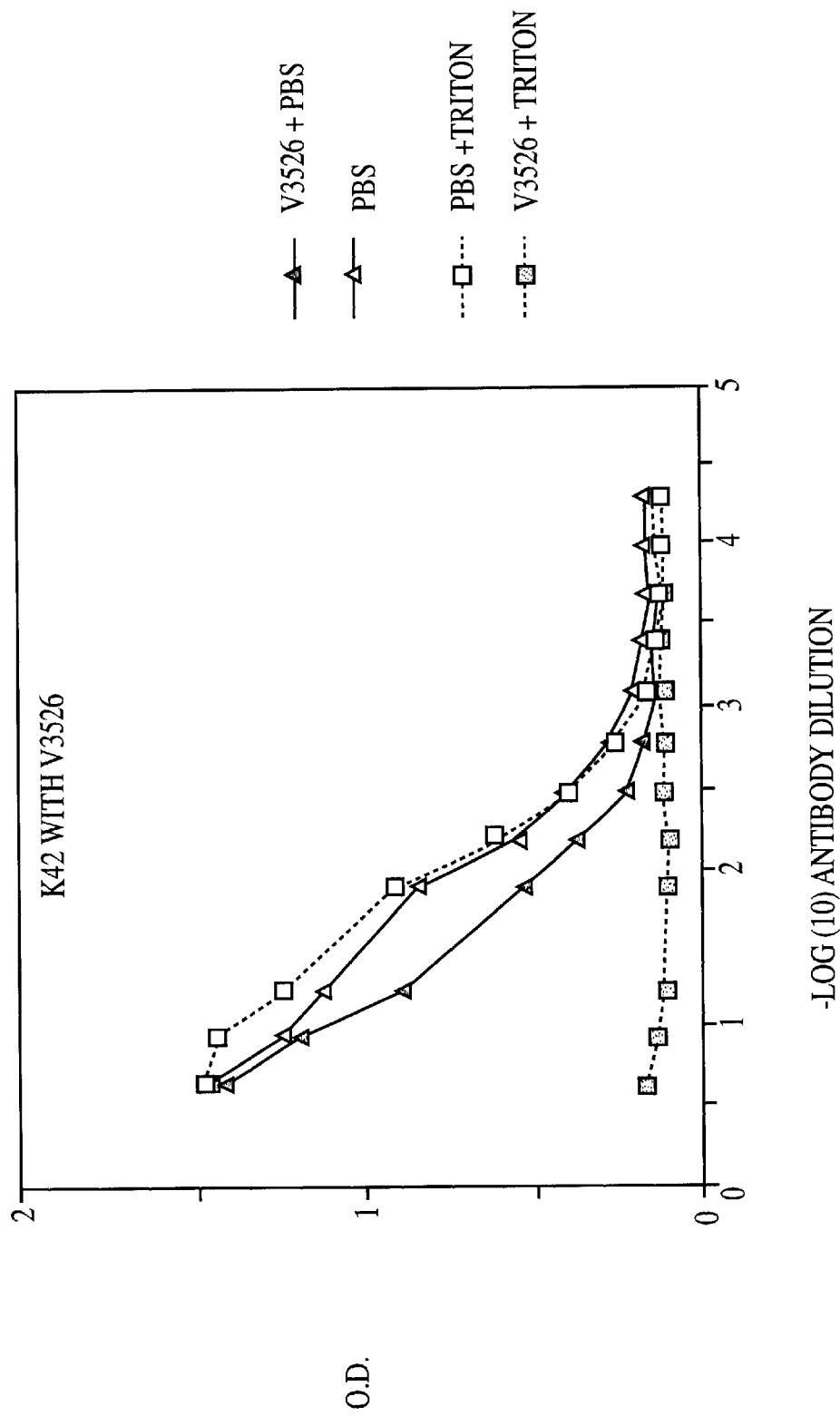
Figure 4D:
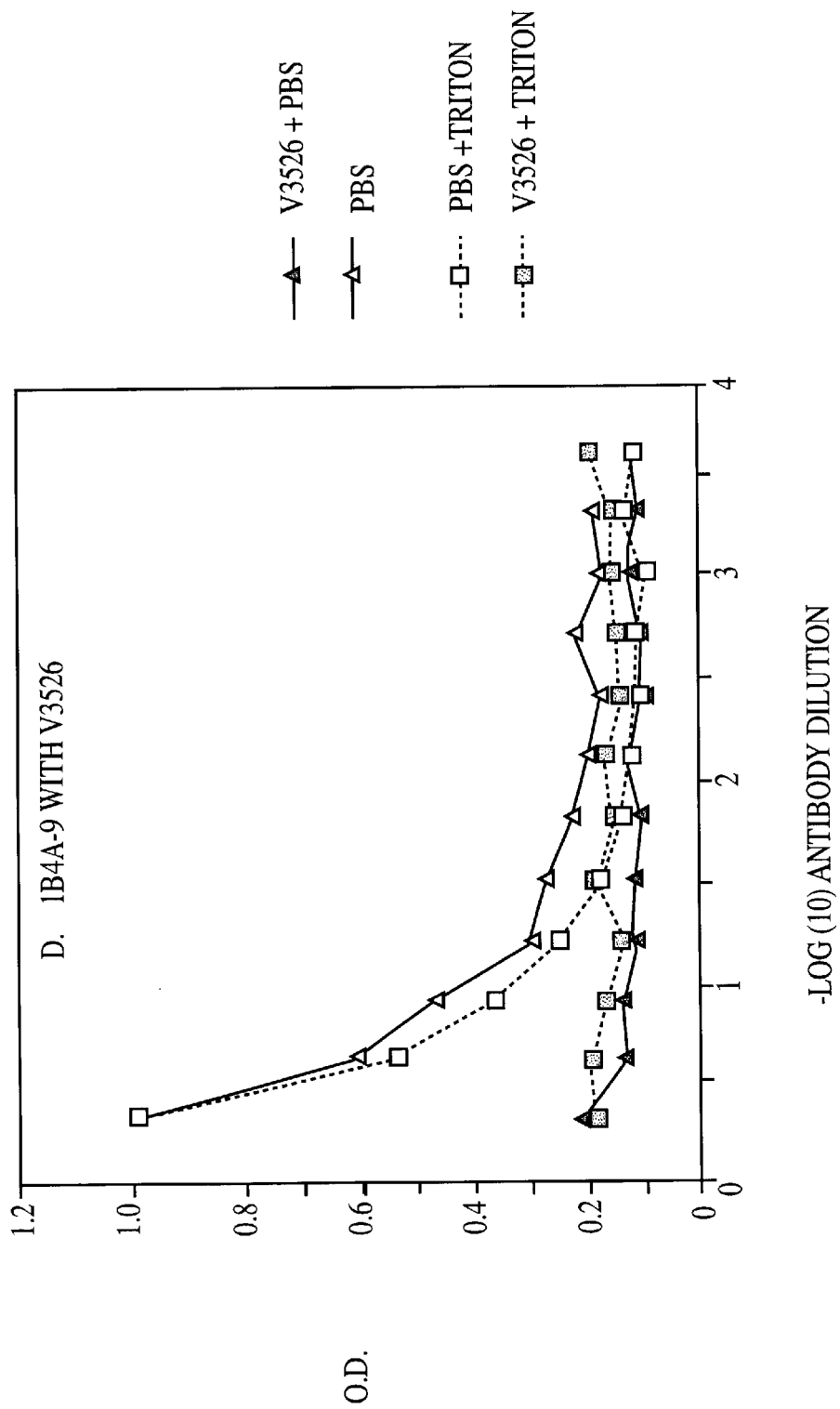

After the observation that K42 mediated significant interference with TC-83 but not V3526 PRNT, a competitive binding assay was done to determine whether K42 had the ability to recognize intact or detergent denatured VEE virus. In order to do so, MAbs were incubated with intact virion or Triton denatured virions and then tested for binding to TC-83 or V3526 in ELISA. K42 was able to competitively bind to Triton-denatured TC-83 or V3526 (FIGS. 4A, C). However, the intact TC-83 or V3526 virions did not decrease the binding of MAb K42 to the antigen-coated plate. The control anti-E1 MAb 1B4A-9, a protective neutralizing antibody, was able to recognize and bind to both denatured and intact TC-83 or V3526 (FIGS. 4B, D).

TABLE 5

Evaluation of Interference with the Induction of Murine Neutralization Antibodies Induced by Different Doses of V3526 in EEE Immune Mice

| Immunogens[a] | PRNT (GMT)[b] | | | |
|---|---|---|---|---|
| primary/secondary | Post Primary | Post Secondary | | Challenge |
| (PFU/mouse) | EEE | EEE | VEE | survival[c] |
| Experiment 1 | | | | |
| EEE/V3526 ($10^5$) | 60 | 170 | 2200 | 9/9 |
| EEE/V3526 ($10^4$) | 120 | 260 | 2940 | 9/10 |
| EEE/V3526 ($10^3$) | 170 | 300 | 120 (7/10) | 9/10 |
| medium/V3526 ($10^5$) | <20 | <20 | 7240 | 10/10 |
| medium/V3526 ($10^4$) | <20 | <20 | 5970 | 9/9 |
| medium/V3526 ($10^3$) | <20 | <20 | 80 (3/10) | 4/10 |
| medium/medium | <20 | <20 | <20 | 0/10 |
| EEE/medium | 170 | 110 | <20 | 8/10 |
| Experiment 2 | | | | |
| EEE/V3526 ($10^6$) | 70 | 90 | 2560 | 10/10 |
| EEE/V3526 ($10^5$) | 110 | 140 | 3150 | 10/10 |
| EEE/V3526 ($10^4$) | 100 | 110 | 1940 | 10/10 |
| medium/V3526 ($10^6$) | <20 | <20 | 4780 | 10/10 |
| medium/V3526 ($10^5$) | <20 | <20 | 5880 | 10/10 |
| medium/V3526 ($10^4$) | <20 | <20 | 5120 | 9/10 |
| medium/medium | <20 | <20 | <20 | 0/10 |
| EEE/medium | 210 | 300 | <20 | 7/10 |

[a]Mice received 0.5% HSA as control medium or EEE vaccine (day 0, 28) s.c. V3526 doses at approximately $10^3$, $10^4$, $10^5$, $10^6$ PFU was administered s.c on day 42 s.c.

[b]Mice were bled on days 35 and 63 and their sera were tested PRNT. Numbers indicated in the parentheses describe the number of responders/ total number of mice tested if less than 10/10. Serum samples from the post primary bleed were screened on heterologous antigen and were not cross-reactive (data not shown). The CNTs of secondary VEE PRNTs titers from experimental groups compare to controls were not reduced greater than three fold.

[c]Mice were challenged with TrD ($10^4$ PFU/mouse) on day 70. Values indicates number of mice survived/mice tested.

TABLE 6

Evaluation of Interference with the TC-83 Vaccine in Mice after Passively Transferring Polyclonal EEE or WEE Antibodies

| Ab/Immunogen[a] | | ELISA (MT)[c] | | PRNT (GMT)[d][e] | | | | | | | | |
|---|---|---|---|---|---|---|---|---|---|---|---|---|
| | | Day 1 | | Day 1 | | 2 weeks | | 4 weeks | | 6 weeks | | |
| primary/secondary | n[b] | VEE | EEE | VEE | EEE | VEE | EEE | VEE | EEE | VEE | EEE | |
| anti-EEE/TC-83 | 10 | 680 | 2420 | <20 | 180 | 30 (5/10) | 110 | 80 (4/10) | 20 | 90 (4/10) | 10 | |
| anti-EEE/medium | 5 | 720 | 2170 | <20 | 140 | 10 | 50 | 10 | 20 | <20 | 10 | |
| anti-HSA/TC-83 | 10 | <100 | <100 | <20 | <20 | 690 (8/10) | <20 | 1370 (8/10) | <20 | 1690 (8/10) | 10 | |
| | n | VEE | WEE | VEE | WEE | VEE | WEE | VEE | WEE | VEE | WEE | |
| anti-WEE/TC-83 | 10 | 720 | 10090 | <20 | 10 | 740 | 10 | 1940 | 10 | 2230 | 10 | |
| anti-WEE/medium | 5 | 720 | 3360 | <20 | 10 | <20 | 10 | <20 | 10 | <20 | 10 | |
| anti-HSA/TC-B3 | 10 | <100 | <100 | <20 | <20 | 690 (8/10) | <20 | 1370 (8/10) | <20 | 1690 (8/10) | 10 | |

[a]Mice received 1 ml of mouse anti-EEE or WEE vaccine polyclonal sera or 0.5% HSA i.p. on day 0. The polyclonal anti-EEE was determined to have a 1280 PRNT titer, 8100 EEE ELISA titer, and 3.12 μg/ml of IgG protein. The polyclonal anti-WEE was determined to have a 10 PRNT, 2700 WEE ELISA titer, and 2.82 μg/ml of IgG protein. The mice were bled on day 1 and 5 hours post-bleed received TC-83 vaccine or medium (0.5% HSA).
[b]Number of mice tested.
[c]Mice were bled on Day 1, and sera were screened by ELISA to determine endpoint titers.
[d]At 6 weeks, statistical values with VEE PRNTs resulted in P = 0.025 with anti-EEE and with P = 0.8 with anti-WEE.
[e]Mice were bled at 2, 4, and 6 week intervals. Their sera were tested for PRNTs. Numbers below the titers indicate number of responders/total number of mice tested.

TABLE 7

Characterization of the MAbs on Various Alphaviruses

| Monoclonal Antibody | Binding in ELISA O.D. (410 mm)[c] Virus Tested | | | | ISOTYPE | SPECIF- ICITY |
|---|---|---|---|---|---|---|
| | EEE | CHIK | VEE | WEE | | |
| 6F10[a] | 0.716 | 3.289 | 4.0 | 0.559 | IgG2a | capsid |
| 15B5[a] | 1.183 | 2.68 | 4.0 | 0.2 | IgG2a | E1 |
| K42[c] | 2.174 | 2.019 | 2.38 | 2.11 | IgG2a | E1 |

[a]The MAb 6F10 and 15B5 were grown in cell culture, and 50 μl was added to ELISA plates.
[b]The MAb K42 was diluted from purified ascites to 1 μg/ml and 50 μl was added to ELISA plates.
[c]An average O.D. of 8 wells is shown for each MAb in ELISAs on each of the viruses listed as described in materials and methods. Values greater than a 0.3 O.D. were considered positive.

TABLE 8

Evaluation of Interference in Mice to TC-83 or V3526 Vaccines after Passively Transfer of Monoclonal Antibodies Experiment 1
A. Ab (50 μg/mouse)/Immunogen[a]

| primary/secondary | ELISA GMT[b] Day 1 VEE | PRNT (GMT)[c] | | | P[d] | Challenge survival[e] |
|---|---|---|---|---|---|---|
| | | 2 weeks VEE | 4 weeks VEE | 6 weeks VEE | | |
| K42/V3526 | 1810 | 730 | 1870 | 2400 | | 11/11 |
| 6F10/V3526 | 370 | 2080 | 3880 | 8910 | | 10/10 |
| 1D6/V3526 | <100 | 1690 | 3620 | 5490 | | 10/10 |
| K42/TC-83 | 1940 | 40 (7/10) | 80 (8/10) | 100 (8/10) | 0.0001 | 7/10 |
| 6F10/TC-83 | 220 | 1810 | 3150 | 4780 | | 10/10 |
| 1D6/TC-83 | <100 | 2080 | 3380 | 4780 | | 10/10 |
| K42/medium | 1560 | <20 | <20 | <20 | | 0/10 |

TABLE 8-continued

Evaluation of Interference in Mice to TC-83 or V3526 Vaccines after Passively Transfer of Monoclonal Antibodies

| 6F10/medium | 300 | <20 | <20 | <20 | | 0/10 |
| 1D6/medium | <100 | <20 | <20 | <20 | | 0/10 |
| anti-EEE/TC-83 | 120 | 90 (3/5) | 110 (3/5) | 140 (3/5) | 0.001 | 2/5 |

Experiment 2
B. Ab (100 μg/mouse)/Immunogen[a]

| primary/secondary | ELISA GMT[b] | PRNT titers (GMT)[c] | | | P[d] | Challenge survival[d] |
| --- | --- | --- | --- | --- | --- | --- |
| | Day 1 VEE | 2 weeks VEE | 4 weeks VEE | 6 weeks VEE | | |
| K42/V3526 | 2700 | 1370 | 2230 | 2390 | 0.0001 | 10/10 |
| 6F10/V3526 | 1000 | 2230 | 5490 | 6300 | | 9/9 |
| 1D6/V3526 | <100 | 2080 | 7240 | 11760 | | 10/10 |
| K42/TC-83 | 1940 | 40 (3/10) | 50 (3/10) | 50 (3/10) | <0.001 | 5/10 |
| 6F10/TC-83 | 2170 | 370 (7/10) | 910 (7/10) | 1040 (7/10) | | 8/10 |
| 1D6/TC-83 | <100 | 2230 (9/10) | 4160 (9/10) | 4780 (9/10) | | 9/10 |
| K42/medium[f] | 2170 | <20 | <20 | <20 | | 2/10 |
| 6F10/medium | 2420 | <20 | <20 | <20 | | 0/10 |
| 1D6/medium | <100 | <20 | <20 | <20 | | 0/10 |
| anti-EEE/TC-83 | 90 | 90 (6/10) | 110 (6/10) | 110 (6/10) | 0.007 | 5/10 |

[a]MAb K42, 6F10 at 50 μg/mouse or 100 μg/mouse were administered on day 0 i.p. Control 0.5 ml of polyclonal anti-EEE and isotype matched 1D6 (50 μg/mouse) were also administered on day 0 i.p. Medium (0.5% HSA), V3526 or TC-83 ($10^4$ PFU/mouse) were administered s.c. on day 1.
[b]Mice were bled on day 1, and sera screened by ELISA to determine endpoint titers.
[c]At 2, 4, and 6 week intervals, mice were re-bled, and their sera tested for PRNT. Numbers indicated in the parentheses describe the number of responders/total number of mice for that specified group.
[d]Statistically significant P values for reduced VEE PRNTs at 6 weeks have been noted.
[e]Mice were challenged with approximately $10^4$ PFU of TrD at 7 weeks. Values indicate number of mice survived/mice tested.
[f]This group of mice had a VEE ELISA GNT titer of 100 at the week 6 bleed.

TABLE 9

Evaluation of Protection to Virulent Trinidad-Donkey in the Presence of Passively Transferred Monoclonal Antibodies in vivo

| | ELISA (GMT)[c] VEE | Challenge survival[d] |
| --- | --- | --- |
| A. MAb (50 μg/mouse)/Immunogen[a] | | |
| Experiment 1 | | |
| K42/TrD | 900 | 2/5 |
| 6F10/TrD | 580 | 0/5 |
| 1D6/TrD | <100 | 0/5 |
| Experiment 2 | | |
| K42/TrD | 720 | 3/5 |
| 6F10/TrD | 370 | 0/5 |
| 1D6/TrD | <100 | 0/5 |
| Experiment 3 | | |
| K42/TrD | 370[e] | 0/10 |
| 1D6/TrD | <100 | 0/10 |
| B. MAb (100 μg/mouse)/Immunogen[b] | | |
| K42/TrD | 5200 | 8/10 |
| 6F10/TrD | 1560 | 0/10 |
| 1D6/TrD | <100 | 0/10 |

[a]Mice received 0.5 ml of 50 μg of K42, 6F10 or 1D6 MAb i.p. on day 0.
[b]Mice received 0.5 ml of 100 μg of K42, 6F10 or 1D6 Mab i.p. on day 0.
[c]Mice were bled on day 1, and their sera screened by ELISA to determine endpoint titers. GMTs are shown for each group.
[d]On day 1, 5 hours post bleed, mice were challenged with $10^4$ PFU of TrD s.c. They were monitored for sickness and death. Values indicate number of survivors/mice tested.

TABLE 9-continued

Evaluation of Protection to Virulent Trinidad-Donkey in the Presence of Passively Transferred Monoclonal Antibodies in vivo

| | ELISA (GMT)[c] VEE | Challenge survival[d] |
| --- | --- | --- |

[e]Two mice from this group had no detectable VEE ELISA titers. These titers (values of 33) were included in the calculation of the GMT.

EXAMPLE 9

Vector Studies

To determine if the phenomenon of interference occurs prior to infection of the cell or at the infected cell, a VEE replicon vector encoding the HA protein from influenza (VRP-HA) was injected into EEE immune mice. A packaged replicon looks like a virus particle and would be susceptible to antibody-mediated interference (clearance mechanisms) that occurs prior to cell infection. After the packaged replicon infects a cell, the influenza protein is made, but VEE virus proteins are not made. As no VEE virus structural proteins are expressed at the cell surface, replicon-infected cells will not be susceptible to interference that is mediated by cross-reactive antibodies like K42. In the presence of EEE antibodies, the VRP-HA induced high-titered influenza antibody responses as measured by ELISA (Table 10). The EEE/VRP-HA immunized mice were protected against influenza challenge (Table 10). In another experiment when the VRP-HA vector was administered to V3526 immune mice, high influenza titers were induced and mice were protected from influenza challenge (Table 11).

TABLE 10

Inability of prior alphavirus cross-reactive, interfering antibodies to inhibit responses to foreign proteins expressed by VEE replicons

| Prior Immunity | GMT Anti-flu Titer[a] after replicon immunization | | Challenge[b] | | |
|---|---|---|---|---|---|
| | 1 | 2 | #Healthy | Sick | Dead |
| Experiment 1 | | | | | |
| None | 216 | 8100 | 9/9 | 0/9 | 0/9 |
| EEE | 184 | 4970 | 9/9 | 0/9 | 9/9 |
| Experiment 2 | | | | | |
| None | 193 | 5220 | 10/10 | 0/10 | 0/10 |
| EEE | 373 | 4190 | 10/10 | 0/10 | 0/10 |

[a]Female BALB/c mice were immunized sc with 0.5 ml inactivated EEE vaccine on day 0 and again on day 28, or sham-immunized with medium. On days 71 and 106, mice were immunized with $1 \times 10^6$ infectious units of a VEE replicon containing an influenza virus HA gene. Anti-influenza antibody responses were measured in ELISA after each of the replicon immunizations. The data are geometric mean titers from groups of 10 mice. Interference was defined as a reduction of at least three-fold in titer.
[b]5 weeks after the second replicon immunization, mice were challenged intranasally with virulent influenza virus. Illness was defined as a loss of at least 10% of body weight for two consecutive days. Mice designated as sick eventually recovered.

TABLE 11

Evaluation of Antibody Responses Elicited by the VRP-HA Vector in V3526 Immune Mice

| Immunogen[a] | | ELISA IgG (GMT) titers[c] [d] | | | Influenza Challenge[e] | | |
|---|---|---|---|---|---|---|---|
| | | post | Influenza | | | | |
| primary/secondary | n[b] | primary VEE | post primary | post secondary[d] | H | S | D |
| V3526/VRP-HA | 10 | 31020 | 520 | 3370 | 10 | | |
| medium/VRP-HA | 9 | <100 | 300 | 2700 | 9 | | |

[a]V3526 vaccine candidate at approximately $10^4$ PFU or medium (0.5% HSA) were administered on day 0. Mice received 2 immunizations of VRP-HA at $10^6$ IU/mouse on days 35 and 73.
[b]Number of mice tested.
[c]Mice were bled on day 28 and sera screened by ELISA to determine endpoint titers for TC-83 reactive antibodies. Mice were also bled on day 63 and 101. Sera were screened by ELISA to determine endpoint titers to influenza.
[d]Statistical values (P > 0.05) were determined from secondary Influenza titers using Student's t-test.
[e]On day 164 mice received $3 \times 10^5$ egg infectious doses of influenza (A/PR/8/34) i.n. Challenged mice were monitored for daily loss of weight. Sickness was defined as a loss of 10% or more of initial body weight for 3 consecutive days (H: healthy; S: sick; D: dead)

EXAMPLE 10

Alphavirus Interference by the K42 Antibody Occurs at the Surface of Infected Cells.

A monoclonal antibody K42 that cross-reacts with different alphaviruses has been demonstrated to interfere with neutralizing antibody responses to TC-83, but not V3526 (as shown above) when the monoclonal antibody is passively administered to mice. The monoclonal antibody binds a site (epitope) on the virus E1 glycoprotein that is exposed on infected cells during virus maturation. This antibody binds to detergent-disrupted TC-83 and V3526 virions, but not intact virions (shown above). The control antibody 1A4A-1 [Roehrig, J. T. and J. H. Mathews (1985) Virol. 142: 347–356] binds a noncryptic epitope that is accessible on intact or denatured virions. Data from complement-mediated lysis experiments suggest that K42 antibody binds to, and causes cell death of, come TC-83-infected Vero cells, but does not do so with V3526-infected cells (Table 12). Together these data suggest that alphavirus interference by the K42 antibody occurs at the surface of infected cells. The ability of V3526 to avoid interference is likely due to the conformational changes in its glycoprotein spikes that may sterically prevent the binding of interfering antibodies. Studies to evaluate interference by other cross-reactive monoclonal antibodies are in progress to identify other viral epitopes that may be involved. We observed that not all alphavirus cross-reactive antibodies mediate vaccine interference using a cross-reactive capsid-specific monoclonal antibody 6F10.

TABLE 12

Ability of Alphavirus Cross-Reactive K42 Antibody to Induce Complement-Mediated Lysis of VEE Virus-Infected Vero Cells

| Antibody | % Lysis of Virus-infected Cells Virus Used to Infect Cells | | |
|---|---|---|---|
| | TC-83 | V3526 | V3000[d] |
| HMAF[a] | 75 | 70 | 100 |
| Anti-E2c[b] | 70 | 70 | 60 |
| K42[c] | 15 | 3 | 100 |

[a]HMAF, hyperimmune mouse ascitic fluids (ATCC, Rockville, MD). Polyclonal antibodies raised against TC-83 virus.
[b]Type-specific virus-neutralizing protective monoclonal antibody [Roehrig, J. T. and J. H. Mathews (1985) Virol. 142: 347–356]
[c]Crossreactive, cross-protective monoclonal antibody to a cryptic epitope on E1 glycoprotein
[d]V300 Trinidad Donkey VEE is the parent of V2536 [Davis, N. et al. (1991) Virology 183: 20–31]

EXAMPLE 11

Prior Immunization with a Cleavage Site Mutant does not Interfere with Immunity to a Second Cleavage Site Mutant W2102 is a live-attenuated potential vaccine candidate for western equine encephalitis virus. W2102 contains a deletion of the furin cleavage site and a glutamate to lysine mutation at position 182 in the E2 glycoprotein. W2102 was generously provided by Dr. Michael Parker, USAMRIID.

BALB/c mice were immunized sc with $1 \times 10^6$ PFU of W2102 or sham-imunized with medium. Five weeks later, mice were immunized with 1e5 PFU of V3526. Analysis of the serum antibody responses to VEE after the first or second vaccine indicated that immunization with W2102 did not interfere with development of neutralizing antibodies to V3526 (Table 13). Furthermore, all of the mice that received V3526 survived subsequent challenge with virulent TrD virus (Table 13). In contrast, only 2/10 mice that received only W2102 survived TrD challenge (Table 13).

TABLE 13

Immunization with a live-attenuated cleavage deletion mutant of WEE does not interfere with immunization to V3526.

| VEE Vaccines Primary/secondary | Post Primary PRNT to VEE | Post Secondary PRNT to VEE | Challenge Survival |
|---|---|---|---|
| medium/W2102 | | | 2/10 |
| medium/V3526 | <20 | 20,400 | 10/10 |
| W2102/V3526 | <20 | 10,900 | 10/10 |

The use of vaccines with cleavage site deletions to overcome alphavirus vaccine interference solves one of the problems observed with the current TC-83 vaccine. However, it is also important to demonstrate that viruses with this mutation will not interfere with each other, which might occur if the E3 proteins that are now included in the glycoprotein spikes have additional cross-reactive sites. Example 11 demonstrates that prior immunization with a WEE cleavage site mutant did not interfere with subsequent development of neutralizing antibody responses to V3526. We were unable to determine if V3526 would interfere with W2102 because W2102 does not induce high-titered WEE neutralizing antibodies and mice are not susceptible to sc challenge with WEE after 6–8 weeks of age.

DISCUSSION

In this study the role of antibodies in alphavirus vaccine interference was evaluated. To study this phenomenon, a murine model (BALB/c mice) was initially established. Although Baker et al. [(1978) *Am. J. Vet. Res.* 30:1627–1631] evaluated models to study CHIK and WEE vaccines respectively, the ability to evaluate interference with these vaccines were limited in BALB/c mice since they did not make high titered PRNT responses to these vaccines.

Passive transfer experiments of EEE immune sera (Table 7) showed that antibodies interfered with the induction of PRNT's to TC-83. The observed interference could not be overcome by increasing the dose of secondary TC-83 immunization ($10^5$–$10^7$ PFU) in EEE immune mice. Although it has been suggested that crossreactive antibodies may be mediating interference [Calisher et al. (1973) *Appl. Micro.* 26:485–488], this is the first extensive study that demonstrated that antibodies mediate alphavirus vaccine interference. Furthermore, the observation that a cross-reactive MAb interfered with TC-83 indicated that a cryptic epitope on the E1 glycoprotein is involved.

Not every cross-reactive antibody interferes with the induction of neutralizing antibody responses to a second alphavirus vaccine as shown by the inability of the cross-reactive anti-capsid MAb 6F10 to mediate interference. 6F10 did not interfere with TC-83 or V3526, possibly because the capsid is accessible to antibody binding only when the virion has been lysed, and no capsid proteins are present prior to lysis on the infected cell.

Results indicated that prior EEE immunity did not mediate significant interference with secondary immunization with V3526. Secondary immunization with V3526 resulted in a two-three fold reduction in VEE secondary PRNTs but the reduction was substantially less than that observed against TC-83. In addition, secondary immunization with V3526 resulted in complete PRNT seroconversion to the vaccine ($10^4$, $10^5$, $10^6$) in EEE and CHIK immune mice and complete protection from TrD challenge. These benefits demonstrate the superior potential and efficacy of V3526 for veterinary and human immunization, and its increased capability to overcome interference in recipients with prior alphavirus immunity.

The studies with TC-83, V3526 and C-84 as the secondary vaccine indicate that live vaccines appear to be more susceptible to interference than inactivated vaccines, and supports similar findings in humans and in animal models [Cole F. and R. McKinney (1971) *Infec. Immun.* 4: 37–42; Calisher et al. 1973, supra]. One possible explanation is that the epitope(s) involved in interference were altered or destroyed by formalin inactivation of C-84. This would also explain similiar observations with the WEE vaccine. However, this would not explain the lack of interference against secondary EEE vaccination, since the EEE vaccine induced responses that interfered with TC-83. Future studies to test the possibility that interfering epitopes on C-84 were altered could be performed using new EEE or WEE vaccines being currently developed.

However, live and inactivated vaccines also differ in their ability to infect cells and in their presentation to the immune system. Whereas both vaccine types will be accessible to the immune system extracellularly and after processing by antigen presenting cells, live alphavirus vaccines also present glycoproteins during virus maturation and budding. One possible explanation of the differences in the interference between TC-83 and C-84 is that interference occurs at the infected cell when the glycoproteins are present at the cell surface. Antibodies can bind to the glycoproteins on infected cells and cause their lysis; however, inactivated vaccines are not susceptible to this mechanism. The observations that live alphavirus vaccines TC-83 and CHIK are both interfered with supports this possibility.

This project determined that an anti-cryptic E1 alphavirus cross-reactive MAb (K42) interferes with the induction of PRNT titers to TC-83 in vivo. This cryptic epitope is exposed to the immune system on infected cells but becomes inaccessible to antibody binding on the intact virion after the virion is packaged into its mature conformation [Schmaljohn et al. (1986) Annual Report, Office of Naval Research]. The ability of K42 to recognize a cryptic epitope on TC-83 was verified by a competition inhibition assay. K42 competitively bound to Triton-denatured TC-83 virus where all the epitopes are exposed but not to intact TC-83 virions. This finding supports the concept that interference with live alphavirus vaccines occurs at the infected cell. K42 may mediate interference by binding to the E1 cryptic epitope on an infected cell and activating complement-mediated lysis via its Fc region.

In contrast, the V3526 vaccine candidate was not as susceptible to interference. The difference in spike formation (PE2/E1 in V3526 vs. E2/E1 of TC-83) may explain the vaccine candidate's ability to overcome interference. The presence of the E3 in the spikes of V3526 and conformational changes due to the mutation at E1:253 may block or change the epitope(s) involved in interference. However, the data indicating that K42 could bind to denatured V3526 in competition assays shows that the E1 cryptic epitope of V3526 has been conserved. The inability of K42 to interfere with V3526-induced responses is more likely due to changes resulting from the lack of PE2 cleavage. The addition of E3 in the spike of V3526 may sterically hinder the binding of K42 to V3526 glycoproteins on infected cells. Additional studies are required to prove that K42 can not bind to V3526 infected cells.

To further evaluate if interference was occurring prior to infection, or at the level of infected cells, a VEE replicon vector was given to mice with pre-existing EEE immunity. In EEE immune animals this vector would be susceptible to interference prior to cell infection, but not after infection. Interference was not observed to the replicon vectored vaccines in these mice. Creation of a VRP double promoter vector co-expressing HA and VEE glycoproteins would be beneficial to prove interference occurs at the infected cell surface.

In summary, we have established a murine model to study interference and evaluated the advantages of V3526 in vaccine interference. Since data showed that crossreactive antibodies are mediating interference, a critical look at the conformational expressions of new alphavirus vaccines is crucial. The demonstration that interference is caused by a MAb that is crossprotective against several alphaviruses presents a challenge to alphavirus vaccine development. For human and animal immunizations scientists need to evaluate whether to produce one crossreactive protective vaccine which is broadly protective against heterologous challenge or multiple alphavirus vaccines that are protective only to homologous strains.

been altered in the furin cleavage site then administering the second alphavirus vaccine such that antibodies produced against said first alphavirus do not interfere with immunity against said second alphavirus.

10. The method of claim 9 wherein said first alphavirus is an altered alphavirus chosen from the group consisting of Venezuelan equine encephalitis, eastern equine encephalitis, western equine encephalitis, chikungunya, Mayaro, O'nyong-nyong, Ross River, and Sindbis.

11. The method of claim 10 wherein said Venezuelan equine encephalitis virus is V3526.

12. The method of claim 11 wherein said subject is an equine.

13. The method of claim 9 wherein said subject is an equine.

14. The method of claim 11 wherein said subject is a human.

15. The method of claim 9 wherein said subject is a human.

16. A method for providing in a subject immunity against two alphaviruses comprising administering to said subject a first and second alphavirus vaccine wherein said first and second alphavirus has been altered in the furin cleavage site.

What is claimed is:

1. A method for inducing in an alphavirus-immune subject neutralizing antibodies against a second alphavirus comprising administering an alphavirus composition comprising said second alphavirus wherein said second alphavirus has been altered in the furin cleavage site such that said second alphavirus is not recognized by interfering antibodies present in said alphavirus-immune recipient.

2. The method according to claim 1 wherein said subject is a mammal.

3. The method according to claim 2 wherein said mammal is a human.

4. The method according to claim 2 wherein said mammal is an equine.

5. The method according to claim 1 wherein said second alphavirus is chosen from the group consisting of Venezuelan equine encephalitis, easternecephalitis, western equine encephalitis, chikunguya, Mayaro, O'nyong-nyong, Ross River, and Sindbis.

6. The method of claim 5 wherein said Venezuelan equine encephalitis virus is V3526.

7. The method of claim 5 wherein said Venezuelan equine encephalitis virus contains a deletion in the furin cleavage site and a viability restoring mutation at glycoprotein E1:253.

8. The method of claim 7 wherein said viability restoring mutation at glycoprotein E1:253 is a serine.

9. A method for providing in a subject immunity against two alphaviruses comprising administering to said subject a first alphavirus vaccine wherein said first alphavirus has 17. A method for inducing in an alphavirus-immune subject neutralizing antibodies against a second alphavirus comprising administering an alphavirus replicon vector comprising sequences encoding one or more alphavirus antigen capable of inducing immunity in said subject against said second alphavirus wherein said alphavirus antigen does not include E1 recognized by interfering antibodies present in said alphavirus-immune recipient.

18. The method of claim 17 wherein said vector is a VEE replicon vector.

19. The method of claim 17 wherein said subject is an equine.

20. The method of claim 17 wherein said subject is a human.

21. The method of claim 18 wherein said subject is an equine.

22. The method of claim 18 wherein said subject is a human.

23. A method for overcoming alphavirus interference in an alphavirus immune subject said method comprising administering to said subject a composition comprising a vector with an encoded antigen capable of inducing an immune response against a second alphavirus wherein expression of said composition does not result in the production of E1 glycoprotein recognized by interfering antibodies in the subject.

24. The method of claim 23 wherein said subject is an equine.

25. The method of claim 23 wherein said subject is a human.

26. A method for overcoming interference in a subject having alphavirus immunity, comprising administering to said subject an alphavirus replicon vector encoding a desired antigen wherein said vector does not express E1 glycoprotein that is recognized by interfering antibodies.

27. The method of claim 26 wherein said subject is an equine.

28. The method of claim 26 wherein said subject is a human.

29. The method of claim 26 wherein said replicon is a Venezuelan equine encephalitis replicon.

30. The method of claim 26 wherein said antigen is hemaglutinin protein from influenza.

* * * * *

```
                            SEQUENCE LISTING

<160> NUMBER OF SEQ ID NOS: 1

<210> SEQ ID NO 1
<211> LENGTH: 4
<212> TYPE: PRT
<213> ORGANISM: Venezuelan Equine Encephalitis Virus TC83

<400> SEQUENCE: 1

Arg Lys Arg Arg
```